United States Patent
Efcavitch et al.

(10) Patent No.: US 9,279,149 B2
(45) Date of Patent: *Mar. 8, 2016

(54) METHODS AND APPARATUS FOR SYNTHESIZING NUCLEIC ACIDS

(71) Applicant: Molecular Assemblies, Inc., San Carlos, CA (US)

(72) Inventors: J. William Efcavitch, San Carlos, CA (US); Suhaib Siddiqi, Burlington, MA (US)

(73) Assignee: Molecular Assemblies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/459,014

(22) Filed: Aug. 13, 2014

(65) Prior Publication Data

US 2014/0363852 A1    Dec. 11, 2014

Related U.S. Application Data

(63) Continuation-in-part of application No. 14/056,687, filed on Oct. 17, 2013, now Pat. No. 8,808,989.

(60) Provisional application No. 61/891,162, filed on Oct. 15, 2013, provisional application No. 61/807,327, filed on Apr. 2, 2013.

(51) Int. Cl.
    *C12Q 1/68* (2006.01)
    *C12P 19/34* (2006.01)

(52) U.S. Cl.
    CPC .............. *C12Q 1/6844* (2013.01); *C12P 19/34* (2013.01); *C12Q 1/6806* (2013.01); *B01J 2219/00596* (2013.01); *B01J 2219/00722* (2013.01)

(58) Field of Classification Search
    CPC ....................................... C12Q 1/6844
    USPC ................................ 435/6.1, 91.1
    See application file for complete search history.

(56) References Cited

U.S. PATENT DOCUMENTS 5,763,594 A    6/1998  Hiatt et al.
5,808,045 A    9/1998  Hiatt et al.
(Continued)

FOREIGN PATENT DOCUMENTS

EP    1 350 842 A2    10/2003
WO    92/10587 A1     6/1992
(Continued)

OTHER PUBLICATIONS

International Search Report and Written Opinion mailed on Aug. 27, 2014, for International Patent Application No. PCT/US2014/033881, filed Apr. 11, 2014 (13 pages).

(Continued)

*Primary Examiner* — Jezia Riley
(74) *Attorney, Agent, or Firm* — Brown Rudnick LLP

(57) ABSTRACT

The invention provides improved methods for synthesizing polynucleotides, such as DNA and RNA, using enzymes and specially designed nucleotide analogs. Using the methods of the invention, specific sequences of polynucleotides can be synthesized de novo, base by base, in an aqueous environment, without the use of a nucleic acid template. Because the nucleotide analogs have an unmodified 3'OH, i.e., as found in "natural" deoxyribose and ribose molecules, the analogs result in natural polynucleotides suitable for incorporation into biological systems.

47 Claims, 16 Drawing Sheets

(56) References Cited

U.S. PATENT DOCUMENTS

| | | | |
|---|---|---|---|
| 5,872,244 | A | 2/1999 | Hiatt et al. |
| 5,990,300 | A | 11/1999 | Hiatt et al. |
| 6,214,987 | B1 | 4/2001 | Hiatt et al. |
| 6,232,465 | B1 | 5/2001 | Hiatt et al. |
| 6,458,127 | B1 | 10/2002 | Truckai et al. |
| 6,664,079 | B2 | 12/2003 | Ju et al. |
| 7,208,172 | B2 | 4/2007 | Birdsall et al. |
| 7,279,563 | B2 | 10/2007 | Kwiatkowski |
| 7,414,116 | B2 | 8/2008 | Milton et al. |
| 7,494,797 | B2 | 2/2009 | Mueller et al. |
| 8,071,755 | B2 | 12/2011 | Efcavitch et al. |
| 8,133,669 | B2 | 3/2012 | Lebedev et al. |
| 8,152,839 | B2 | 4/2012 | Buiser et al. |
| 8,460,910 | B2 | 6/2013 | Smith et al. |
| 8,623,628 | B2 | 1/2014 | Ost et al. |
| 8,808,989 | B1 * | 8/2014 | Efcavitch et al. ............. 435/6.1 |
| 2004/0043396 | A1 | 3/2004 | Mueller et al. |
| 2006/0127443 | A1 | 6/2006 | Helmus |
| 2007/0036905 | A1 | 2/2007 | Kramer |
| 2009/0186771 | A1 | 7/2009 | Siddiqi et al. |
| 2011/0081647 | A1 | 4/2011 | Siddiqi et al. |
| 2011/0124529 | A1 | 5/2011 | Brennan |
| 2011/0201002 | A1 | 8/2011 | Gelfand et al. |
| 2012/0040340 | A1 | 2/2012 | Efcavitch et al. |
| 2013/0189743 | A1 | 7/2013 | Balasubramanian et al. |

FOREIGN PATENT DOCUMENTS

| | | |
|---|---|---|
| WO | 94/14972 A1 | 7/1994 |
| WO | 2005/005667 A2 | 1/2005 |
| WO | 2005/024010 A1 | 3/2005 |
| WO | 2005/026184 A2 | 3/2005 |
| WO | 2005/080605 A2 | 9/2005 |
| WO | 2006/007207 A2 | 1/2006 |
| WO | 2007/022493 A2 | 2/2007 |
| WO | 2007/062160 A2 | 5/2007 |
| WO | 2007/147110 A2 | 12/2007 |
| WO | 2008/046602 A2 | 4/2008 |
| WO | 2008/046609 A2 | 4/2008 |
| WO | 2008/144315 A1 | 11/2008 |
| WO | 2008/144544 A1 | 11/2008 |
| WO | 2009/124254 A1 | 10/2009 |

OTHER PUBLICATIONS

International Search Report and Written Opinion mailed on Jan. 21, 2015, for International Patent Application No. PCT/IB2014/061673, filed May 23, 2014 (16 pages).

Sugiyama T, Ishii S, Saito K, Yamamoto J, Isogai T, Ota T. Preparation of sensitive and specific oligonucleotide probes tailed using terminal transferase and dITP. Biotechniques. Mar. 2000;28(3):486-90.

European Search Report for Application No. EP 14 16 9758, with the Date of completion of the search of Jan. 12, 2015 (17 pages).

Barone AD, Chen C, McGall GH, Rafii K, Buzby PR, Dimeo JJ. Novel nucleoside triphosphate analogs for the enzymatic labeling of nucleic acids. Nucleoside, Nucleotides and Nucleic Acids 2001;20(4-7):1141-5.

Bentley DR, Balasubramanian S, Swerdlow HP, Smith GP, Milton J, Brown CG, et al. Accurate whole human genome sequencing using reversible terminator chemistry.Nature 2008;456:53-9.

Bowers et al., Molecular Biology of Terminal Transferase, Nature Methods, vol. 6, (2009) p. 593-95.

Bowers J, Mitchell J, Beer E, Buzby PR, Causey M, Efcavitch JW, Jarosz M, Krzymanska-Olejnik E, Kung L, Lipson D, Lowman GM, Marappan S, McInerney P, Plat A, Roy A, Siddiqi SM, Steinmann K, Thompson JF. Virtual terminator nucleotides for next-generation DNA sequencing. Nature Methods 2009;6(8):593-95.

Carlson R, The changing economics of DNA synthesis. Nature Biotechnol. 2009;27:1091-4.

Caruthers MH. Gene Synthesis Machines: DNA chemistry and its Uses. Science 1985;230(4723):281-5.

Efcavitch JW. Automated System for the Optimized Chemical Synthesis of Oligodeoxyribonucleotides. In: Schlesinger DH, editor. Macromolecular Sequencing and Synthesis. New York: Alan R Liss, Inc.; 1988. p. 221-34.

Flickinger JL, Gebeyehu G, Haces A, Rashtchian A. Differential incorporation of biotinylated nucleotides by terminal deoxynucleotidyl transferase. Nucleic Acids Res 1992;20(9):2382.

Guo J, Xu N, Li Z, Zhang S, Wu J, Hyun Kim D, Marma MS, Meng Q, Cao H, Li X, Shi S, Yu L, Kalachikov S, Russo JJ, Turro NJ, Ju J. Four-color DNA sequencing with 3'-Omodifiednucleotide reversible terminators and chemically cleavable fluorescent dideoxynucleotides. Proc. Natl. Acad. Sci. USA 2008;105:9145-50.

Horakova P, Macickova-Cahova H, Pivonkova H, Spacek J, Havran L, Hocek M, Fojta M. Tail-labelling of DNA probes using modified deoxynucleotide triphosphates and terminal deoxynucleotidyl transferase. Application in electrochemical DNA hybridization and protein-DNA binding assays. Org Biomol Chem 2011;9(5):1366-71.

Lashkari DA, Hunicke-Smith SP, Norgren RM, Davis RW, Brennan T. An automated multiplex oligonucleotide synthesizer: development of high-throughput, low-cost DNA synthesis. Proc Natl Acad Sci USA. 1995 ;92(17):7912-15.

Leconte AM, Patel MP, Sass LE, McInerney P, Jarosz M, Kung L, Bowers JL, Buzby PR, Efcavitch JW, Romesberg FE. Directed evolution of DNA polymerases for next generation sequencing. Angew Chem Int Ed Engl. 2010;49 (34):5921-24.

Lee CC, Snyder TM, Quake SR. A Microfluidic Oligonucleotide Synthesizer. Nucleic Acids Res 2010;38:2514-21.

LeProust EM, Peck BJ, Spirin K, MCuen HB, Moore B, Namsaraev E, Caruthers MH. Synthesis of high-quality libraries of long (150mer) oligonucleotides by a novel depurination controlled process. Nucleic Acids Res 2010;38(8):2522-40.

Litosh VA, Wu W, Stupi BP, Wang J, Morris SE, Hersh N, Metzker ML. Improved nucleotide selectivity and termination of 3?-OH unblocked reversible terminators by molecular tuning of 2-nitrobenzyl alkylated HOMedU triphosphates. Nucleic Acid Res 2011;39:e39.

Matzas M, Stahler PF, Kefer N, Siebelt N, Boisguerin V, Leonard JT, et al. Next Generation Gene Synthesis by targeted retrieval of bead-immobilized, sequence verified DNA clones from a high throughput pyrosequencing device. Nat Biotechnol. 2010;28(12):1291-1294.

Metzker ML, Raghavachari R, Richards S, Jacutin SE, Civitello A, Burgess K, Gibbs RA. Termination of DNA synthesis by novel 3'-modifieddeoxyribonucleoside 5'-triphosphates. Nucleic Acids Res 1994;22:4259-67.

Motea EA, Berdis AJ. Terminal deoxynucleotidyl transferase: The story of a misguided DNA polymerase. Biochimica et Biophysica Acta 2010;1804:1151-6.

Zahid M, Kim B, Hussain R, Amin R, Park SH. DNA nanotechnology: a future perspective. Nanoscales Res Lett. 2013;8:119-32.

International Search Report and Written Opinion mailed on Sep. 30, 2014, for International Patent Application No. PCT/US2014/033811, filed Apr. 11, 2014 (12 pages).

Carr PA, Park JS, Lee Y-J, Yu T, Zhang S, Jacobson JM. Protein-mediated error correction for de novo DNA Synthesis. Nucleic Acids Research 2004;vol. 32(20):e162.

Chen F, Gaucher EA, Leal NA, Hutter D, Havemann SA, Govindarajan S, Ortlund EA, Benner SA. Reconstructed evolutionary adaptive paths give polymerases accepting reversible terminators for sequencing and SNP detection. Proc Natl Acad Sci U S A. Feb. 2, 2010;107(5):1948-53.

Damiani G, Scovassi I, Romagnoli S, Palla+ E, Bertazzoni U, Sgaramella V. Sequence analysis of heteropolymeric DNA synthesized in vitro by the enzyme terminal deoxynucleotidyl transferase and cloned in *Escherichia coli.* Nucleic Acids Res 1982;10(20):6401-10.

Gordon SR, Stanley EJ, Wolf S, Toland A, Wu SJ, Hadidi D, Mills JH, Baker D, Pultz IS, Siegel JB. Computational design of an ?-gliadin peptidase. J Am Chem Soc. Dec. 19, 2012;134(50):20513-20.

Hoard DE, Robert L, Ratliff D, Lloyd W, Newton Hayes F. Heteropolydeoxynucleotides synthesized with terminal deoxyribonucleotidyl transferase. J of Biol Chem 1969;244(19):5363-73.

(56) References Cited

OTHER PUBLICATIONS

Hutter D, Kim MJ, Karalkar N, Leal NA, Chen F, Guggenheim E, Visalakshi V, Olejnik J, Gordon S, Benner SA. Labeled nucleoside triphosphates with reversibly terminating aminoalkoxyl groups. Nucleosides Nucleotides Nucleic Acids. Nov. 2010;29(11):879-95.

Ju J, Kim DH, Bi L, Meng Q, Bai X, Li Z, Li X, Marma MS, Shi S, Wu J, Edwards JR, Romu A, Turro NJ. Four-color DNA sequencing by synthesis using cleavable fluorescent nucleotide reversible terminators. Proc Natl Acad Sci U S A. Dec. 26, 2006;103(52):19635-40.

Kuan WL, Joy J, Mee NF, Perlyn KZ, Wen TS, Nguen T, James J, Chai E, Flowtow H, Crasta S, Chua K, Peng NS, Hill J. Generation of active bovine Terminal Deoxynucleotidyl Transferase (TdT) in *E. coli*. Biochem. Insights. 2010;3:41-6.

Li X, Traganos F, Melamed MR, Darzynkiewicz Z. Single-step procedure for labeling DNA strand breaks with fluorescein- or BODIPY-conjugated deoxynucleotides: detection of apoptosis and bromodeoxyuridine incorporation. Cytometry 1995;20(2):172-80.

Life Technologies [Internet]. Carlsbad: Life Technologies Inc.; c 2013. Oligo Minimum Yield Guarantee; [cited Dec. 1, 2013]. Available from: http://www.lifetechnologies.com/us/en/home/products-and-services/product-types/primers-oligos-nucleotides/invitrogen-custom-dna-oligos/oligo-ordering-details/oligo-minimum-yield-guarantee.html.

Minhaz Ud-Dean SM. A theoretical model for template-free synthesis of long DNA sequence. Syst Synth Biol. 2009;2:67-73.

Nitta Y, Ogino M, Yoshimura Y, Fujimoto K. Synthesis of a photoresponsive alpha-dideoxyuridine triphosphate derivative. Nucleic Acids Symp Ser (Oxf). 2008;(52):293-4.

Romain F, Barbosa I, Gouge J, Rougeon F, Delarue M. Conferring a template-dependent polymerase activity to terminal deoxynucleotidyltransferase by mutations in the Loop1 region. Nucleic Acids Res. 2009;37(14):4642-56.

Schott H, Schrade H. Single-step elongation of oligodeoxynucleotides using terminal deoxynucleotidyl transferase. Eur J Biochem 1984;143:613-20.

Siegel JB, Zanghellini A, Lovick HM, Kiss G, Lambert AR, St Clair JL, Gallaher JL, Hilvert D, Gelb MH, Stoddard BL, Houk KN, Michael FE, Baker D. Computational design of an enzyme catalyst for a stereoselective bimolecular Diels-Alder reaction. Science. Jul. 16, 2010;329(5989):309-13.

Sleight SC, Bartley BA, Lieviant JA, Sauro HM. In-Fusion BioBrick assembly and re-engineering. Nucleic Acids Res. May 2010;38(8):2624-36.

Wu SJ, Eiben CB, Carra JH, Huang I, Zong D, Liu P, Wu CT, Nivala J, Dunbar J, Huber T, Senft J, Schokman R, Smith MD, Mills JH, Friedlander AM, Baker D, Siegel JB. Improvement of a potential anthrax therapeutic by computational protein design. J Biol Chem. Sep. 11, 2011;286(37):32586-92.

Yang B, Gathy KN, Coleman MS. Mutational Analysis of Residues in the Nucleotide Binding Domain of Human Terminal Deoxynucleotidyl Transferase. J. Mol. Biol. Apr. 22, 1994; 269(16):11859-68.

International Search Report and Written Opinion for PCT/US2014/033811, mailed Sep. 30, 2014.

Kosuri S, Church GM. Large-scale de novo DNA synthesis: technologies and applications. Nat Methods. May 2014;11 (5):499-507.

Alexandrova LA, Jasko MV, Belobritskaya EE, Chudinov AV, Mityaeva ON, Nasedkina TV, Zasedatelev AS, Kukhanova MK. New triphosphate conjugates bearing reporter groups: labeling of DNA fragments for microarray analysis. Bioconjug Chem. May-Jun. 2007;18(3):886-93.

Auriol J, Chevrier D, Guesdon JL. Acetoxy-acetylaminofluorene-modified dGTP can be used to label oligonucleotides or DNA enzymatically. Mol Cell Probes Apr. 1997;11(2):113-21.

Beaucage SL, Caruthers, MH. Studies on Nucleotide Chemistry V. Deoxynucleoside Phosphoramidites—A New Class of Key Intermediates for Deoxypolynucleotide Synthesis. Tetrahedron Lett. 1981;22:1859-62.

Bi L, Kim DH, Ju J. Design and synthesis of a chemically cleavable fluorescent nucleotide, 3'-O-allyl-dGTP-allyl-bodipy-FL-510, as a reversible terminator for DNA sequencing by synthesis. J Am Chem Soc. Mar. 1, 2006;128 (8):2542-3.

Bollum FJ. Terminal Deoxynucleotidyl Transferase. In: Boyer PD, editor. The Enzymes. vol. 10. New York: Academic Press; 1974. p. 148.

Boule J-B, Johnson E, Rougeo F, Papinicolaou. High-Level Expression of Murine Terminal Deoxynucleotidyl Transferase in *Escherichia coli* at Low Temparature and Overexpressing argU tRNA. Mol Biotechnology 1998;10:199-208.

Büssow K, Nordhoff E, Lübbert C, Lehrach H, Walter G. A human cDNA library for high-throughput protein expression screening. Genomics. Apr. 1, 2000;65(1):1-8.

Chang LMS, Bollum FJ. Molecular Biology of terminal Transferase. CRC Crit Rev Biochem. 1986;21(1):27-52.

Chow DC, Chilikoti A. Surface-initiated enzymatic polymerization of DNA. Langmuir 2007; 23:11712-7.

Chow DC, Lee W-K, Zauscher S, Chilikoti A. Enzymatic fabrication of DNA nanostructures: Extension of a self-assembled oligonucleotide monolayer on gold arrays. J Am Chem Soc 2005;127:14122-3.

Deibel MR, Liu CG, Barkley MD. Fluorimetric assay for terminal deoxynucleotidyl transferase activity. Anal Biochem 1985;144(2):336-46.

Delarue M, Boulé JB, Lescar J, Expert-Bezançon N, Jourdan N, Sukumar N, Rougeon F, Papanicolaou C. Crystal structures of a template-independent DNA polymerase: murine terminal deoxynucleotidyltransferase. Embo J. 2002;21(3):427-39.

Figeys D, Renborg A, Dovichi NJ. Labeling of double-stranded DNA by ROX-dideoxycytosine triphosphate using terminal deoxynucleotidyl transferase and separation by capillary electrophoresis. Anal Chem 1994;66(23):4382-3.

Gouge J, Rosario S, Romain F, Beguin P, Delarue M. Structures of Intermediates along the Catalytic Cycle of Terminal Deoxynucleotidyltransferase: Dynamical Aspects of the Two-Metal Ion Mechanism. J Mol Biol. Nov. 15, 2013;425 (22):4334-52.

Ikeda Y, Kawahara S-I, Yoshinari K, Fujita S, Taira K. Specifc 3'-terminal modification of DNA with a novel nucleoside analogue that allows a covalent linkage of a nuclear localization signal and enhancement of DNA stability. ChemBioChem 2005;6:297-303.

Kasahara Y, Kitadume S, Morihiro K, Kuwahara M, Ozaki H, Sawai H, Imanishi T, Obika S. Effect of 3'-end capping of aptamer with various 2',4'-bridged nucleotides: Enzymatic post-modification toward a practical use of polyclonal aptamers. Bioorg Med Chem Lett. Mar. 1, 2010;20(5):1626-9.

Kosuri S, Eroshenko N, Leproust EM, Super M, Way J, Li JB, Church GM. Scalable gene synthesis by selective amplification of DNA pools from high-fidelity microchips. Nat Biotechnol. Dec. 2010;28(12):1295-9.

Matteucci MD, Caruthers MH. Studies on Nucleotide Chemistry IV. Synthesis of Deoxyoligonucleotides on a Polymer Support. J. Amer. Chem. Soc. 1981;103:3185-91.

Meng Q, Kim DH, Bai X, Bi L, Turro NJ, Ju J. Design and synthesis of a photocleavable fluorescent nucleotide 3'-O-allyl-dGTP-PC-Bodipy-FL-510 as a reversible terminator for DNA sequencing by synthesis. J Org Chem. Apr. 14, 2006;71(8):3248-52.

Muller R, Drosdziok W, Rajewsky MF. Enzymatic synthesis of double-stranded DNA containing radioactively labeled O6-ethylguanine as the only modified base. Carcinogenesis 1981;2(4):321-7.

Sørensen RS, Okholm AH, Schaffert D, Bank Kodal AL, Gothelf KV, Kjems J. Enzymatic Ligation of Large Biomolecules to DNA. ACS Nano 2013;7(9):8098-104.

Tjong V, Yu H, Hucknall A, Rangarajan S, Chilkoti A. Amplified on-chip fluorescence detection of DNA hybridization by surface-initiated enzymatic polymerization. Anal Chem 2011;83:5153-59.

Zhou G, Sylvester JE, Wu D, Veach DR, Kron SJ. A magnetic bead-based protein kinase assay with dual detection techniques. Anal. Biochem. 2011;408:5-11.

* cited by examiner n = 2 or 3
X = O, NH, CH₂, S

TCEP or DTT n = 2 or 3
X = O, NH, CH₂, S

TCEP or DTT n = 2 or 3
X = O, NH, CH$_2$, S

TCEP or DTT n = 2 or 3
X = O, NH, CH$_2$, S

TCEP or DTT n = 2 or 3
X = O, NH, CH$_2$, S

TCEP or DTT n = 2 or 3
X = O, NH, CH$_2$, S

TCEP or DTT n = 1 - 4
X = O, S, NH, CH$_2$

X = O, S, NH, CH$_2$ n = 1 - 4
X = O, S, NH, CH$_2$ n = 1 - 4
X = O, S, NH, CH$_2$ n = 1 - 4
X = O, S, NH, CH$_2$

SEQUENCE LISTING

```
<160> NUMBER OF SEQ ID NOS: 6

<210> SEQ ID NO 1
<211> LENGTH: 520
<212> TYPE: PRT
<213> ORGANISM: Bos taurus

<400> SEQUENCE: 1

Met Ala Gln Gln Arg Gln His Gln Arg Leu Pro Met Asp Pro Leu Cys
1               5                  10                  15

Thr Ala Ser Ser Gly Pro Arg Lys Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
    50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
        115                 120                 125

Glu Ile Thr Gly Lys His Gln Leu Val Val Arg Thr Asp Tyr Ser Ala
    130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
        195                 200                 205

Leu Lys Ser Leu Pro Phe Thr Ile Ile Ser Met Lys Asp Thr Glu Gly
    210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
        275                 280                 285

Met Ser Asp Lys Thr Leu Lys Phe Thr Lys Met Gln Lys Ala Gly Phe
    290                 295                 300

Leu Tyr Tyr Glu Asp Leu Val Ser Cys Val Thr Arg Ala Glu Ala Glu
```

```
                305                 310                 315                 320
Ala Val Gly Val Leu Val Lys Glu Ala Val Trp Ala Phe Leu Pro Asp
                325                 330                 335
Ala Phe Val Thr Met Thr Gly Gly Phe Arg Arg Gly Lys Lys Ile Gly
                340                 345                 350
His Asp Val Asp Phe Leu Ile Thr Ser Pro Gly Ser Ala Glu Asp Glu
                355                 360                 365
Glu Gln Leu Leu Pro Lys Val Ile Asn Leu Trp Glu Lys Lys Gly Leu
                370                 375                 380
Leu Leu Tyr Tyr Asp Leu Val Glu Ser Thr Phe Glu Lys Phe Lys Leu
385                 390                 395                 400
Pro Ser Arg Gln Val Asp Thr Leu Asp His Phe Gln Lys Cys Phe Leu
                405                 410                 415
Ile Leu Lys Leu His His Gln Arg Val Asp Ser Ser Lys Ser Asn Gln
                420                 425                 430
Gln Glu Gly Lys Thr Trp Lys Ala Ile Arg Val Asp Leu Val Met Cys
                435                 440                 445
Pro Tyr Glu Asn Arg Ala Phe Ala Leu Leu Gly Trp Thr Gly Ser Arg
                450                 455                 460
Gln Phe Glu Arg Asp Ile Arg Arg Tyr Ala Thr His Glu Arg Lys Met
465                 470                 475                 480
Met Leu Asp Asn His Ala Leu Tyr Asp Lys Thr Lys Arg Val Phe Leu
                485                 490                 495
Lys Ala Glu Ser Glu Glu Ile Phe Ala His Leu Gly Leu Asp Tyr
                500                 505                 510
Ile Glu Pro Trp Glu Arg Asn Ala
                515                 520

<210> SEQ ID NO 2
<211> LENGTH: 1923
<212> TYPE: DNA
<213> ORGANISM: Bos taurus

<400> SEQUENCE: 2
ctcttctgga gataccactt gatggcacag cagaggcagc atcagcgtct tcccatggat      60
ccgctgtgca cagcctcctc aggccctcgg aagaagagac ccaggcaggt gggtgcctca     120
atggcctccc ctcctcatga catcaagttt caaaatttgg tcctcttcat tttggagaag     180
aaaatgggaa ccacccgcag aaacttcctc atggagctgg ctcgaaggaa aggtttcagg     240
gttgaaaatg agctcagtga ttctgtcacc cacattgtag cagaaaacaa ctctggttca     300
gaggttctcg agtggcttca ggtacagaac ataagagcca gctcgcagct agaactcctt     360
gatgtctcct ggctgatcga agtatgggga gcaggaaaac cagtggagat tacaggaaaa     420
caccagcttg ttgtgagaac agactattca gctaccccaa acccaggctt ccagaagact     480
ccaccacttg ctgtaaaaaa gatctcccag tacgcgtgtc aaagaaaaac cactttgaac     540
aactataacc acatattcac ggatgccttt gagatactgg ctgaaaattc tgagtttaaa     600
gaaaatgaag tctcttatgt gacatttatg agagcagctt ctgtacttaa atctctgcca     660
ttcacaatca tcagtatgaa ggatacagaa ggaattccct gcctggggga caaggtgaag     720
tgtatcatag aggaaattat tgaagatgga gaaagttctg aagttaaagc tgtgttaaat     780
gatgaacgat atcagtcctt caaactcttt acttctgttt ttggagtggg actgaagaca     840
tctgagaaat ggttcaggat ggggttcaga tctctgagta aaataatgtc agacaaaacc     900
```

-continued

```
ctgaaattca caaaaatgca gaaagcagga tttctctatt atgaagacct tgtcagctgc    960
gtgaccaggg ccgaagcaga ggcggttggc gtgctggtta agaggctgt gtgggcattt    1020
ctgccggatg ccttttgtcac catgacagga ggattccgca ggggtaagaa gattgggcat   1080
gatgtagatt ttttaattac cagcccagga tcagcagagg atgaagagca acttttgcct   1140
aaagtgataa acttatggga aaaaaaggga ttacttttat attatgacct tgtggagtca    1200
acatttgaaa agttcaagtt gccaagcagg caggtggata cttagatca ttttcaaaaa    1260
tgctttctga ttttaaaatt gcaccatcag agagtagaca gtagcaagtc caaccagcag    1320
gaaggaaaga cctggaaggc catccgtgtg gacctggtta tgtgcccta cgagaaccgt     1380
gcctttgccc tgctaggctg gactggctcc cggcagtttg agagagacat ccggcgctat   1440
gccacacacg agcggaagat gatgctggat aaccacgctt tatatgacaa gaccaagagg    1500
gtatttctca agcggaaag tgaagaagaa atctttgcac atctgggatt ggactacatt     1560
gaaccatggg aaagaaatgc ttaggagaaa gctgtcaact tttttctttt ctgttctttt    1620
tttcaggtta gacaaattat gcttcatatt ataatgaaag atgccttagt caagtttggg    1680
attctttaca ttttaccaag atgtagatt cttctagaaa taagtagttt tggaaacgtg     1740
atcaggcacc ccctgggtta tgctctggca agccatttgc aggactgatg tgtagaactc    1800
gcaatgcatt ttccatagaa acagtgttgg aattggtggc tcatttccag ggaagttcat    1860
caaagcccac tttgcccaca gtgtagctga atactgtat acttgccaat aaaaatagga     1920
aac                                                                  1923
```

```
<210> SEQ ID NO 3
<211> LENGTH: 465
<212> TYPE: PRT
<213> ORGANISM: Escherichia coli

<400> SEQUENCE: 3

Met Phe Thr Arg Val Ala Asn Phe Cys Arg Lys Val Leu Ser Arg Glu
1               5                   10                  15

Glu Ser Glu Ala Glu Gln Ala Val Ala Arg Pro Gln Val Thr Val Ile
            20                  25                  30

Pro Arg Glu Gln His Ala Ile Ser Arg Lys Asp Ile Ser Glu Asn Ala
        35                  40                  45

Leu Lys Val Met Tyr Arg Leu Asn Lys Ala Gly Tyr Glu Ala Trp Leu
    50                  55                  60

Val Gly Gly Gly Val Arg Asp Leu Leu Leu Gly Lys Lys Pro Lys Asp
65                  70                  75                  80

Phe Asp Val Thr Thr Asn Ala Thr Pro Glu Gln Val Arg Lys Leu Phe
                85                  90                  95

Arg Asn Cys Arg Leu Val Gly Arg Arg Phe Arg Leu Ala His Val Met
            100                 105                 110

Phe Gly Pro Glu Ile Ile Glu Val Ala Thr Phe Arg Gly His His Glu
        115                 120                 125

Gly Asn Val Ser Asp Arg Thr Thr Ser Gln Arg Gly Gln Asn Gly Met
    130                 135                 140

Leu Leu Arg Asp Asn Ile Phe Gly Ser Ile Glu Glu Asp Ala Gln Arg
145                 150                 155                 160

Arg Asp Phe Thr Ile Asn Ser Leu Tyr Tyr Ser Val Ala Asp Phe Thr
                165                 170                 175

Val Arg Asp Tyr Val Gly Gly Met Lys Asp Leu Lys Asp Gly Val Ile
            180                 185                 190
```

Arg Leu Ile Gly Asn Pro Glu Thr Arg Tyr Arg Glu Asp Pro Val Arg
              195                 200                 205

Met Leu Arg Ala Val Arg Phe Ala Ala Lys Leu Gly Met Arg Ile Ser
        210                 215                 220

Pro Glu Thr Ala Glu Pro Ile Pro Arg Leu Ala Thr Leu Leu Asn Asp
225                 230                 235                 240

Ile Pro Pro Ala Arg Leu Phe Glu Gly Ser Leu Lys Leu Leu Gln Ala
                245                 250                 255

Gly Tyr Gly Tyr Glu Thr Tyr Lys Leu Leu Cys Glu Tyr His Leu Phe
                260                 265                 270

Gln Pro Leu Phe Pro Thr Ile Thr Arg Tyr Phe Thr Glu Asn Gly Asp
            275                 280                 285

Ser Pro Met Glu Arg Ile Ile Glu Gln Val Leu Lys Asn Thr Asp Thr
290                 295                 300

Arg Ile His Asn Asp Met Arg Val Asn Pro Ala Phe Leu Phe Ala Ala
305                 310                 315                 320

Met Phe Trp Tyr Pro Leu Leu Glu Thr Ala Gln Lys Ile Ala Gln Glu
                325                 330                 335

Ser Gly Leu Thr Tyr His Asp Ala Phe Ala Leu Ala Met Asn Asp Val
                340                 345                 350

Leu Asp Glu Ala Cys Arg Ser Leu Ala Ile Pro Lys Arg Leu Thr Thr
            355                 360                 365

Leu Thr Arg Asp Ile Trp Gln Leu Gln Leu Arg Met Ser Arg Arg Gln
        370                 375                 380

Gly Lys Arg Ala Trp Lys Leu Leu Glu His Pro Lys Phe Arg Ala Ala
385                 390                 395                 400

Tyr Asp Leu Leu Ala Leu Arg Ala Glu Val Glu Arg Asn Ala Glu Leu
                405                 410                 415

Gln Arg Leu Val Lys Trp Trp Gly Phe Gln Val Ser Ala Pro Pro
            420                 425                 430

Asp Gln Lys Gly Met Leu Asn Glu Leu Asp Glu Glu Pro Ser Pro Arg
            435                 440                 445

Arg Arg Thr Arg Arg Pro Arg Lys Arg Ala Pro Arg Arg Glu Gly Thr
        450                 455                 460

Ala
465

<210> SEQ ID NO 4
<211> LENGTH: 1398
<212> TYPE: DNA
<213> ORGANISM: Escherichia coli

<400> SEQUENCE: 4
atttttaccc gagtcgctaa ttttgccgc aaggtgctaa gccgcgagga aagcgaggct      60
gaacaggcag tcgcccgtcc acaggtgacg gtgatcccgc gtgagcagca tgctatttcc     120
cgcaaagata tcagtgaaaa tgccctgaag gtaatgtaca ggctcaataa agcgggatac     180
gaagcctggc tggttggcgg cggcgtgcgc gacctgttac ttggcaaaaa gccgaaagat     240
tttgacgtaa ccactaacgc cacgcctgag caggtgcgca aactgttccg taactgccgc     300
ctggtgggtc gccgtttccg tctggctcat gtaatgtttg gcccggagat tatcgaagtt     360
gcgaccttcc gtggacacca cgaaggtaac gtcagcgacc gcacgacctc ccaacgcggg     420
caaaacggca tgttgctgcg cgacaacatt ttcggctcca tcgaagaaga cgcccagcgc     480

```
cgcgatttca ctatcaacag cctgtattac agcgtagcgg attttaccgt ccgtgattac      540
gttggcggca tgaaggatct gaaggacggc gttatccgtc tgattggtaa cccggaaacg      600
cgctaccgtg aagatccggt acgtatgctg cgcgcggtac gttttgccgc caaattgggt      660
atgcgcatca gcccggaaac cgcagaaccg atccctcgcc tcgctaccct gctgaacgat      720
atcccaccgg cacgcctgtt tgaagaatcg cttaaactgc tacaagcggg ctacggttac      780
gaaacctata agctgttgtg tgaatatcat ctgttccagc cgctgttccc gaccattacc      840
cgctacttca cggaaaatgg cgacagcccg atggagcgga tcattgaaca ggtgctgaag      900
aataccgata cgcgtatcca taacgatatg cgcgtgaacc cggcgttcct gtttgccgcc      960
atgttctggt acccactgct ggagacggca cagaagatcg cccaggaaag cggcctgacc     1020
tatcacgacg ctttcgcgct ggcgatgaac gacgtgctgg acgaagcctg ccgttcactg     1080
gcaatcccga aacgtctgac gacattaacc cgcgatatct ggcagttgca gttgcgtatg     1140
tcccgtcgtc agggtaaacg cgcatggaaa ctgctggagc atcctaagtt ccgtgcggct     1200
tatgacctgt tggccttgcg agctgaagtt gagcgtaacg ctgaactgca cgtctggtg      1260 aaatggtggg gtgagttcca ggtttccgcg ccaccagacc aaaaagggat gctcaacgag     1320
ctggatgaag aaccgtcacc gcgtcgtcgt actcgtcgtc cacgcaaacg cgcaccacgt     1380
cgtgagggta ccgcatga                                                   1398
```

```
<210> SEQ ID NO 5
<211> LENGTH: 349
<212> TYPE: PRT
<213> ORGANISM: Escherichia coli

<400> SEQUENCE: 5

Gly Ser His Met Ser Tyr Gln Lys Val Pro Asn Ser His Lys Glu Phe
1               5                   10                  15

Thr Lys Phe Cys Tyr Glu Val Tyr Asn Glu Ile Lys Ile Ser Asp Lys
            20                  25                  30

Glu Phe Lys Glu Lys Arg Ala Ala Leu Asp Thr Leu Arg Leu Cys Leu
        35                  40                  45

Lys Arg Ile Ser Pro Asp Ala Glu Leu Val Ala Phe Gly Ser Leu Glu
    50                  55                  60

Ser Gly Leu Ala Leu Lys Asn Ser Asp Met Asp Leu Cys Val Leu Met
65                  70                  75                  80

Asp Ser Arg Val Gln Ser Asp Thr Ile Ala Leu Gln Phe Tyr Glu Glu
                85                  90                  95

Leu Ile Ala Glu Gly Phe Glu Gly Lys Phe Leu Gln Arg Ala Arg Ile
            100                 105                 110

Pro Ile Ile Lys Leu Thr Ser Asp Thr Lys Asn Gly Phe Gly Ala Ser
        115                 120                 125

Phe Gln Cys Asp Ile Gly Phe Asn Asn Arg Leu Ala Ile His Asn Thr
    130                 135                 140

Leu Leu Leu Ser Ser Tyr Thr Lys Leu Asp Ala Arg Leu Lys Pro Met
145                 150                 155                 160

Val Leu Leu Val Lys His Trp Ala Lys Arg Lys Gln Ile Asn Ser Pro
                165                 170                 175

Tyr Phe Gly Thr Leu Ser Ser Tyr Gly Tyr Val Leu Met Val Leu Tyr
            180                 185                 190
```

```
Tyr Leu Ile His Val Ile Lys Pro Pro Val Phe Pro Asn Leu Leu Leu
            195                 200                 205

Ser Pro Leu Lys Gln Glu Lys Ile Val Asp Gly Phe Asp Val Gly Phe
            210                 215                 220

Asp Asp Lys Leu Glu Asp Ile Pro Pro Ser Gln Asn Tyr Ser Ser Leu
225                 230                 235                 240

Gly Ser Leu Leu His Gly Phe Phe Arg Phe Tyr Ala Tyr Lys Phe Glu
                245                 250                 255

Pro Arg Glu Lys Val Val Thr Phe Arg Arg Pro Asp Gly Tyr Leu Thr
                260                 265                 270

Lys Gln Glu Lys Gly Trp Thr Ser Ala Thr Glu His Thr Gly Ser Ala
                275                 280                 285

Asp Gln Ile Ile Lys Asp Arg Tyr Ile Leu Ala Ile Glu Asp Pro Phe
            290                 295                 300

Glu Ile Ser His Asn Val Gly Arg Thr Val Ser Ser Ser Gly Leu Tyr
305                 310                 315                 320

Arg Ile Arg Gly Glu Phe Met Ala Ala Ser Arg Leu Leu Asn Ser Arg
                325                 330                 335

Ser Tyr Pro Ile Pro Tyr Asp Ser Leu Phe Glu Glu Ala
                340                 345

<210> SEQ ID NO 6
<211> LENGTH: 1047
<212> TYPE: DNA
<213> ORGANISM: Escherichia coli

<400> SEQUENCE: 6
ggcagccata tgagctatca gaaagtgccg aacagccata agaatttac caaattttgc      60
tatgaagtgt ataacgaaat taaaattagc gataaagaat ttaaagaaaa acgcgcggcg    120
ctggataccc tgcgcctgtg cctgaaacgc attagcccgg atgcggaact ggtggcgttt    180
ggcagcctgg aaagcggcct ggcgctgaaa acagcgata tggatctgtg cgtgctgatg     240
gatagccgcg tgcagagcga taccattgcg ctgcagtttt atgaagaact gattgcggaa    300
ggctttgaag gcaaatttct gcagcgcgcg cgcattccga ttattaaact gaccagcgat    360
accaaaaacg gctttggcgc gagctttcag tgcgatattg gctttaacaa ccgcctggcg    420
attcataaca ccctgctgct gagcagctat accaaactgg atgcgcgcct gaaaccgatg    480
gtgctgctgg tgaaacattg ggcgaaacgc aaacagatta acagcccgta ttttggcacc    540
ctgagcagct atggctatgt gctgatggtg ctgtattatc tgattcatgt gattaaaccg    600
ccggtgtttc cgaacctgct gctgagcccg ctgaaacagg aaaaaattgt ggatggcttt    660
gatgtgggct tgatgataa actggaagat attccgccga ccagaacta tagcagcctg     720
ggcagcctgc tgcatggctt ttttcgcttt tatgcgtata aatttgaacc gcgcgaaaaa    780
gtggtgacct tcgccgccc ggatggctat ctgaccaaac aggaaaaagg ctggaccagc    840
gcgaccgaac ataccggcag cgcggatcag attattaaag atcgctatat tctggcgatt    900
gaagatccgt ttgaaattag ccataacgtg ggccgcaccg tgagcagcag cggcctgtat    960
cgcattcgcg gcgaatttat ggcggcgagc cgcctgctga acagccgcag ctatccgatt   1020
ccgtatgata gcctgtttga agaagcg                                       1047
```

METHODS AND APPARATUS FOR SYNTHESIZING NUCLEIC ACIDS

RELATED APPLICATIONS

This application is a continuation-in-part of U.S. application Ser. No. 14/056,687, filed on Oct. 17, 2013 which claims priority to U.S. Provisional Application Nos. 61/807,327, filed Apr. 2, 2013, and 61/891,162, filed Oct. 15, 2013, all of which are incorporated by reference in their entireties.

FIELD OF THE INVENTION

The invention relates to methods and apparatus for synthesizing polynucleotides (de novo) with a desired sequence and without the need for a template. As such, the invention provides the capacity to make libraries of polynucleotides of varying sequence and varying length for research, genetic engineering, and gene therapy.

BACKGROUND

Genetic engineering requires tools for determining the content of genetic material as well as tools for constructing desired genetic materials. The tools for determining the content of genetic material have made it possible to sequence an entire human genome in about one day for under $1,000. (See Life Technologies, *Press Release: Benchtop Ion Proton™ Sequencer*, Jan. 10, 2012). In contrast, the tools for constructing desired genetic materials, e.g., de novo DNA synthesis, have not improved at the same pace. As a point of reference, over the past 25 years, the cost (per base) of de novo small nucleic acid synthesis has dropped 10-fold, while the cost (per base) of nucleic acid sequencing has dropped over 10,000,000-fold. The lack of progress in DNA synthesis now limits the pace of translational genomics, i.e., whereby the role of individual sequence variations are determined and used to develop therapeutic treatments.

Currently, most de novo nucleic acid sequences are synthesized using solid phase phosphoramidite-techniques developed more than 30 years ago. The technique involves the sequential de-protection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligo production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., *Nucleic Acids Res.*, vol. 38(8), p. 2522-2540, (2010), incorporated by reference herein in its entirety). Thus, there is a need for more efficient and cost-effective methods for oligonucleotide synthesis.

SUMMARY

The invention provides improved methods for nucleic acid synthesis. Methods of the invention provide faster and longer de novo synthesis of polynucleotides. As such, the invention dramatically reduces the overall cost of synthesizing custom nucleic acids. Methods of the invention are directed to template-independent synthesis of polynucleotides by using a nucleotidyl transferase enzyme to incorporate nucleotide analogs having an unmodified 3' hydroxyl coupled to an inhibitor by a cleavable linker. Because of the inhibitor, synthesis pauses with the addition of each new base, whereupon the linker is cleaved, separating the inhibitor and leaving a polynucleotide that is essentially identical to a naturally occurring nucleotide (i.e., is recognized by the enzyme as a substrate for further nucleotide incorporation).

The invention additionally includes an apparatus that utilizes methods of the invention for the production of custom polynucleotides. An apparatus of the invention includes one or more bioreactors providing aqueous conditions and a plurality of sources of nucleotide analogs. The bioreactor may be e.g., a reservoir, a flow cell, or a multi-well plate. Starting from a solid support, the polynucleotides are grown in the reactor by adding successive nucleotides via the natural activity of a nucleotidyl transferase, e.g., a terminal deoxynucleotidyl transferase (TdT) or any other enzyme which elongates DNA or RNA strands without template direction. Upon cleavage of the linker, a natural polynucleotide is exposed on the solid support. Once the sequence is complete, the support is cleaved away, leaving a polynucleotide essentially equivalent to that found in nature. In some embodiments, the apparatus is designed to recycle nucleotide analog solutions by recovering the solutions after nucleotide addition and reusing solutions for subsequence nucleotide addition. Thus, less waste is produced, and the overall cost per base is reduced as compared to state-of-the-art methods. In certain embodiments, a bioreactor may include a microfluidic device and/or use inkjet printing technology.

Other aspects of the invention are apparent to the skilled artisan upon consideration of the following figures and detailed description.

DETAILED DESCRIPTION

Figure 1A:
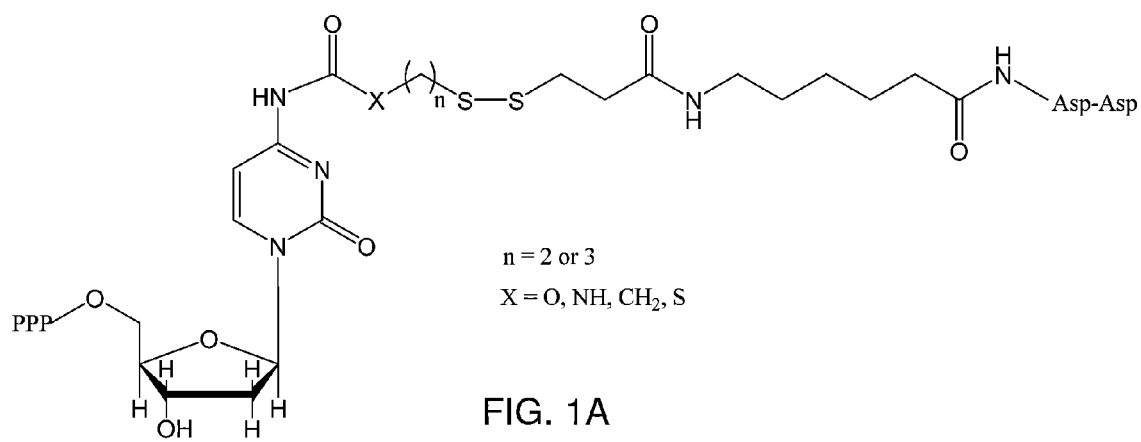
FIG. 1A shows a genus of deoxycytidine triphosphate (dCTP) analogs having a cleavable terminator linked at the N-4 position.

The invention provides improved methods for synthesizing polynucleotides, such as DNA and RNA, using enzymes and nucleic acid analogs. Using the disclosed methods, specific sequences of polynucleotides can be synthesized de novo, base by base, in an aqueous environment, without the use of a nucleic acid template. Additionally, because the nucleotide analogs have an unmodified 3' hydroxyls, i.e., as found in "natural" deoxyribose and ribose molecules, the analogs result in "natural" nucleotides when an inhibitor, attached via a cleavable linker, is removed from the base. Other nucleotide analogs can also be used which, for example, include self-eliminating linkers, or nucleotides with modified phosphate groups. In most instances, the blocking group is designed to not leave behind substantial additional molecules, i.e., designed to leave behind "scarless" nucleotides that are recognized as "natural" nucleotides by the enzyme. Thus, at the conclusion of the synthesis, upon removal of the last blocking group, the synthesized polynucleotide is chemically and structurally equivalent to the naturally-occurring polynucleotide with the same sequence. The synthetic polynucleotide can, thus, be incorporated into living systems without concern that the synthesized polynucleotide will interfere with biochemical pathways or metabolism.

The process and analogs of the current invention can be used for the non-templated enzymatic synthesis of useful oligo- and oligodeoxynucleotides especially of long oligonucleotides (<5000 nt). Products can be single strand or partially double strand depending upon the initiator used. The synthesis of long oligonucleotides requires high efficiency incorporation and high efficiency of reversible terminator removal. The initiator bound to the solid support consists of a short, single strand DNA sequence that is either a short piece of the user defined sequence or a universal initiator from which the user defined single strand product is removed.

In one aspect, the disclosed methods employ commercially-available nucleotidyl transferase enzymes, such as terminal deoxynucleotidyl transferase (TdT), to synthesize polynucleotides from nucleotide analogs in a step-by-step fashion. The nucleotide analogs are of the form:

NTP-linker-inhibitor wherein NTP is a nucleotide triphosphate (i.e., a dNTP or an rNTP), the linker is a cleavable linker between the pyridine or pyrimidine of the base, and the inhibitor is a group that prevents the enzyme from incorporating subsequent nucleotides. At each step, a new nucleotide analog is incorporated into the growing polynucleotide chain, whereupon the enzyme is blocked from adding an additional nucleotide by the inhibitor group. Once the enzyme has stopped, the excess nucleotide analogs can be removed from the growing chain, the inhibitor can be cleaved from the NTP, and new nucleotide analogs can be introduced in order to add the next nucleotide to the chain. By repeating the steps sequentially, it is possible to quickly construct nucleotide sequences of a desired length and sequence. Advantages of using nucleotidyl transferases for polynucleotide synthesis include: 1) 3'-extension activity using single strand (ss) initiating primers in a template-independent polymerization, 2) the ability to extend primers in a highly efficient manner resulting in the addition of thousands of nucleotides, and 3) the acceptance of a wide variety of modified and substituted NTPs as efficient substrates. In addition, the invention can make use of an initiator sequence that is a substrate for nucleotidyl transferase. The initiator is attached to a solid support and serves as a binding site for the enzyme. The initiator is preferably a universal initiator for the enzyme, such as a homopolymer sequence and is recyclable on the solid support, the formed oligonucleotide being cleavable from the initiator.

Methods of the invention are well-suited to a variety of applications that currently use synthetic nucleic acids, e.g., phosphoramidite-synthesized DNA oligos. For example, polynucleotides synthesized with the methods of the invention can be used as primers for nucleic acid amplification, hybridization probes for detection of specific markers, and for incorporation into plasmids for genetic engineering. However, because the disclosed methods produce longer synthetic strings of nucleotides, at a faster rate, and in an aqueous environment, the disclosed methods also lend themselves to high-throughput applications, such as screening for expression of genetic variation in cellular assays, as well as synthetic biology. Furthermore, the methods of the invention will provide the functionality needed for next-generation applications, such as using DNA as synthetic read/write memory, or creating macroscopic materials synthesized completely (or partially) from DNA.

The invention and systems described herein provide for synthesis of polynucleotides, including deoxyribonucleic acids (DNA) and ribonucleic acids (RNA). While synthetic pathways for "natural" nucleotides, such as DNA and RNA, are described in the context of the common nucleic acid bases, e.g., adenine (A), guanine (G), cytosine (C), thymine (T), and uracil(U), it is to be understood that the methods of the invention can be applied to so-called "non-natural" nucleotides, including nucleotides incorporating universal bases such as 3-nitropyrrole 2'-deoxynucloside and 5-nitroindole 2'-deoxynucleoside, alpha phosphorothiolate, phosphorothioate nucleotide triphosphates, or purine or pyrimidine conjugates that have other desirable properties, such as fluorescence. Other examples of purine and pyrimidine bases include pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. In some instances, it may be useful to produce nucleotide sequences having unreactive, but approximately equivalent bases, i.e., bases that do not react with other proteins, i.e., transcriptases, thus allowing the influence of sequence information to be decoupled from the structural effects of the bases.

Analogs

The invention provides nucleotide analogs having the formula NTP-linker-inhibitor for synthesis of polynucleotides in an aqueous environment. With respect to the analogs of the form NTP-linker-inhibitor, NTP can be any nucleotide triphosphate, such as adenosine triphosphate (ATP), guanosine triphosphate (GTP), cytidine triphosphate (CTP), thymidine triphosphate (TTP), uridine triphosphate (UTP), nucleotide triphosphates, deoxyadenosine triphosphate (dATP), deoxyguanosine triphosphate (dGTP), deoxycytidine triphosphate (dCTP), deoxythymidine triphosphate (dTTP), or deoxyuridine triphosphate (dUTP).

The linker can be any molecular moiety that links the inhibitor to the NTP and can be cleaved. For example, the linkers can be cleaved by adjusting the pH of the surrounding environment. The linkers may also be cleaved by an enzyme that is activated at a given temperature, but inactivated at another temperature. In some embodiments, the linkers include disulfide bonds.

Linkers may, for example, include photocleavable, nucleophilic, or electrophilic cleavage sites. Photocleavable linkers, wherein cleavage is activated by a particular wavelength of light, may include benzoin, nitroveratryl, phenacyl, pivaloyl, sisyl, 2-hydroxy-cinamyl, coumarin-4-yl-methyl, or 2-nitrobenzyl based linkers.

Figure 15:
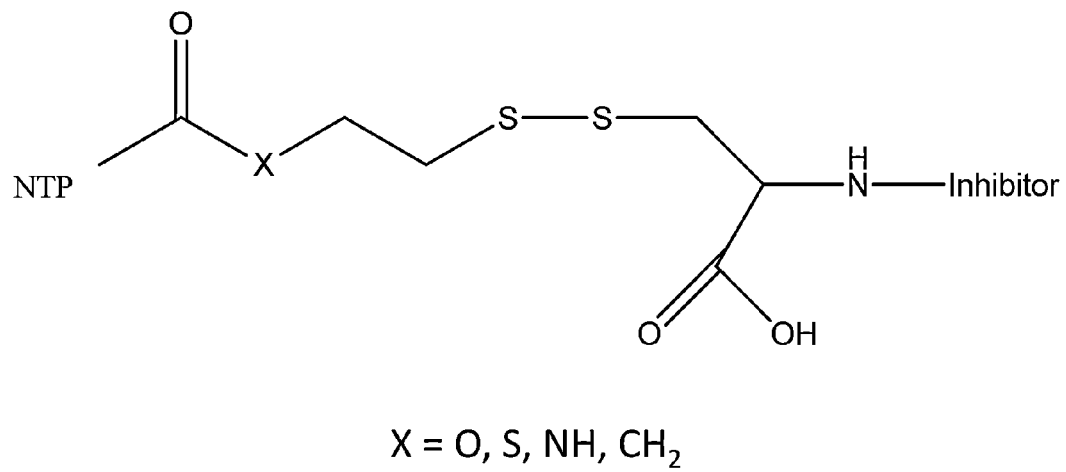
FIG. 15 shows an exemplary nucleotide analog with a cleavable linker comprising a cysteine residue.

Examples of nucleophilic cleavage sites include fluoride ion cleavable silicon-oxygen bonds or esters which may be cleaved in a basic solution. Electrophilically cleaved linkers may include acid induced cleavage sites which may comprise trityl, tert-butyloxycarbonyl groups, acetal groups, and p-alkoxybenzyl esters and amides. In certain aspects, a cleavable linker may include a cysteine residue as shown in FIG. 15.

The linker can be attached, for example, at the N4 of cytosine, the N3 or O4 of thymine, the N2 or N3 of guanine, and the N6 of adenine, or the N3 or O4 of uracil because attachment at a carbon results in the presence of a residual scar after removal of the polymerase-inhibiting group. The linker is typically on the order of at least about 10 Angstroms long, e.g., at least about 20 Angstroms long, e.g., at least about 25 Angstroms long, thus allowing the inhibitor to be far enough from the pyridine or pyrimidine to allow the enzyme to bind the NTP to the polynucleotide chain via the attached sugar backbone. In some embodiments, the cleavable linkers are self-cyclizing in that they form a ring molecule that is particularly non-reactive toward the growing nucleotide chain.

In certain aspects, a cleavable linker may include a variable number of methylene bridges on the NTP or the inhibitor side of a disulfide bond, including, for example, 1, 2, 3, or 4 methylene bridges as shown in FIGS. 14 and 16A-C. These methylene bridges may be used to increase the space between the NTP and the inhibitor. As noted above, the length of the cleavable linker may be selected in order to prevent the inhibitor from interfering with coupling of the NTP to the synthesized polynucleotide. In some embodiments of the invention, the distance of the charged group to the NTP plays an important role in the effectiveness of inhibiting a subsequent nucleotide incorporation.

For example, in some embodiments using a charged moiety as an inhibitor, the charged moiety may be from about 5 to about 60 bonds away from the NTP. In some other embodiments, the charged moiety of the inhibitor may be from about 10 to about 40 bonds away from the NTP. In some other embodiments, the charged moiety of the inhibitor can be from about 10 to about 35 bonds away from the NTP. In some other embodiments, the charged moiety of the inhibitor may be from about 10 to about 30 bonds away from the NTP. In some other embodiments, the charged moiety of the inhibitor is from about 10 to about 20 bonds away from the NTP. The number of bonds between the charged moiety and the NTP may be increased by including additional methylene bridges.

Figure 16A:
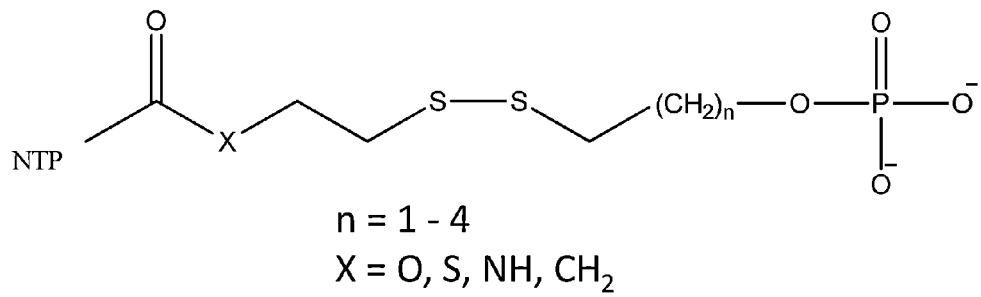
FIG. 16A shows an exemplary nucleotide analog with an anionic inhibitor comprising a single phosphate group.
Figure 16B:
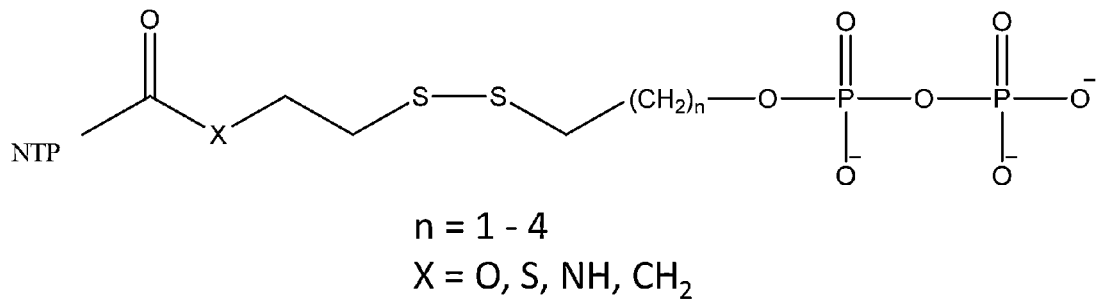
FIG. 16B shows an exemplary nucleotide analog with an anionic inhibitor comprising two phosphate groups.
Figure 16C:
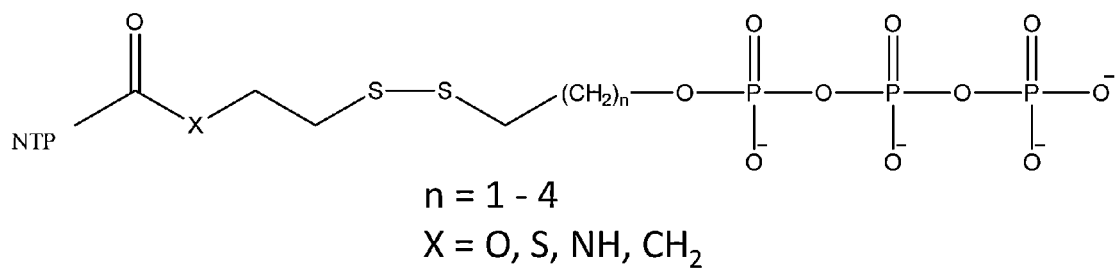
FIG. 16C shows an exemplary nucleotide analog with an anionic inhibitor comprising three phosphate groups.

The nucleotide analogs can include any moiety linked to the NTP that inhibits the coupling of subsequent nucleotides by the enzyme. The inhibitory group can be a charged group, such as a charged amino acid, or the inhibitory group can be a group that becomes charged depending upon the ambient conditions. In some embodiments, the inhibitor may include a moiety that is negatively charged or capable of becoming a negatively charged. For example, an inhibitor may include a chain of phosphate groups (e.g., 1, 2, or 3, phosphates) as shown in FIGS. 16A-C, wherein additional phosphates increase the overall anionic charge of the inhibitor. In other embodiments, the inhibitor group is positively charged or capable of becoming positively charged. In some other embodiments, the inhibitor is an amino acid or an amino acid analog. The inhibitor may be a peptide of 2 to 20 units of amino acids or analogs, a peptide of 2 to 10 units of amino acids or analogs, a peptide of 3 to 7 units of amino acids or analogs, a peptide of 3 to 5 units of amino acids or analogs. In some embodiments, the inhibitor includes a group selected from the group consisting of Glu, Asp, Arg, His, and Lys, and a combination thereof (e.g., Arg, Arg-Arg, Asp, Asp-Asp, Asp, Glu, Glu-Glu, Asp-Glu-Asp, Asp-Asp-Glu or AspAspAspAsp, etc.). Peptides or groups may be combinations of the same or different amino acids or analogs. In certain embodiments, a peptide inhibitor may be acetylated to discourage errant bonding of free amino groups. The inhibitory group may also include a group that reacts with residues in the active site of the enzyme thus interfering with the coupling of subsequent nucleotides by the enzyme. The inhibitor may have a charged group selected from the group consisting of —COO, —NO$_2$, —PO$_4$, —PO$_3$, —SO$_2$, or —NR$_3$ where each R may be H or an alkyl group. In other embodiments, the inhibitor moiety does not comprise a —PO4 group.

Figure 1B:
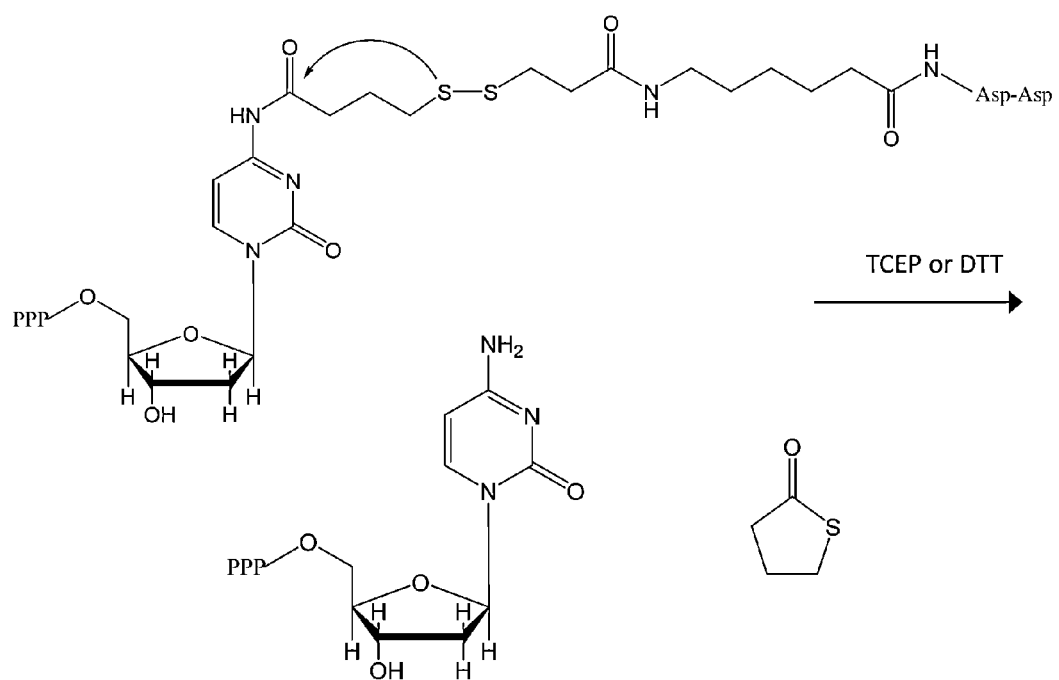
FIG. 1B shows cleavage of the cleavable terminator from a dCTP analog of FIG. 1A to achieve a "natural" dCTP and a cyclic leaving molecule.

An example of a nucleotide analog of the type NTP-linker-inhibitor is shown in FIG. 1A. The analog in FIG. 1A includes an inhibitory (-Asp-Asp-) group linked to the N4 position of dCTP through a disulfide (—S—S—) bond while providing an unblocked, unmodified 3'-OH on the sugar ring. The linker is constructed such that all linker atoms (including the 2nd incorporation-inhibiting moiety) can be removed, thereby allowing the nascent DNA strand to revert to natural nucleotides. As shown in FIG. 1B, an aqueous reducing agent, such as tris(2-carboxyethyl) phosphine (TCEP) or dithiothreitol (DTT), can be used to cleave the —S—S— bond, resulting in the loss of the inhibitor function (deblocking). As shown in FIG. 1B, a self-cyclizing linker can be incorporated, resulting in a cyclic oxidized tetrahydrothiophene leaving group that is easily removed from the reagent solution at the conclusion of nucleotide synthesis.

Exemplary schemes for synthesizing dCTP analogs of FIG. 1A are shown below in Schemes 1A and 1B:

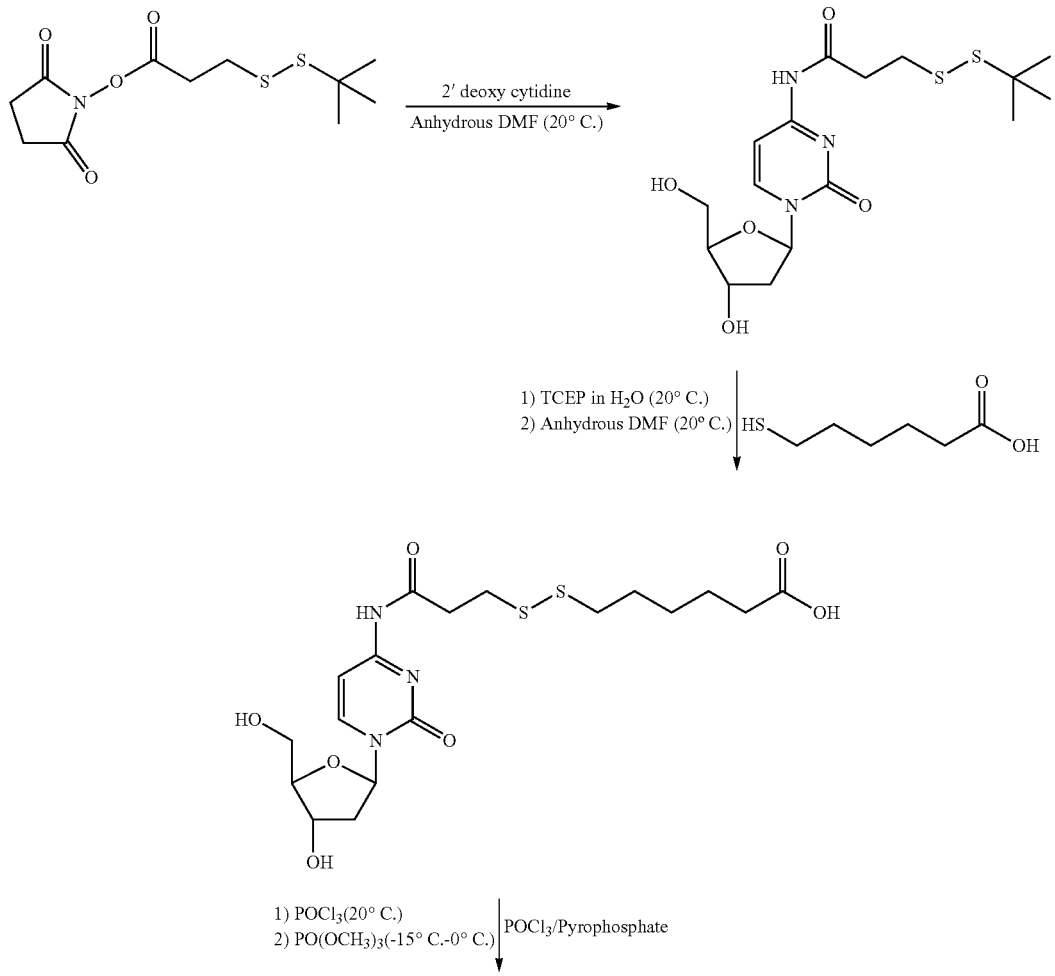

Scheme 1A

-continued
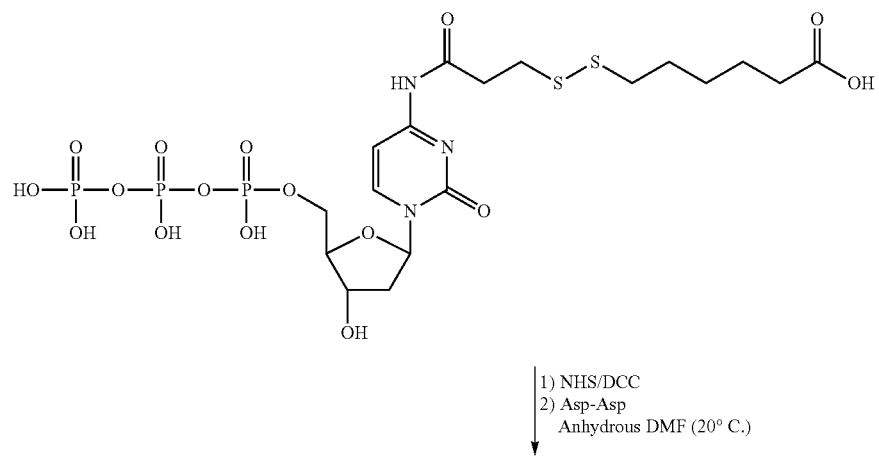
1) NHS/DCC
2) Asp-Asp
Anhydrous DMF (20° C.)
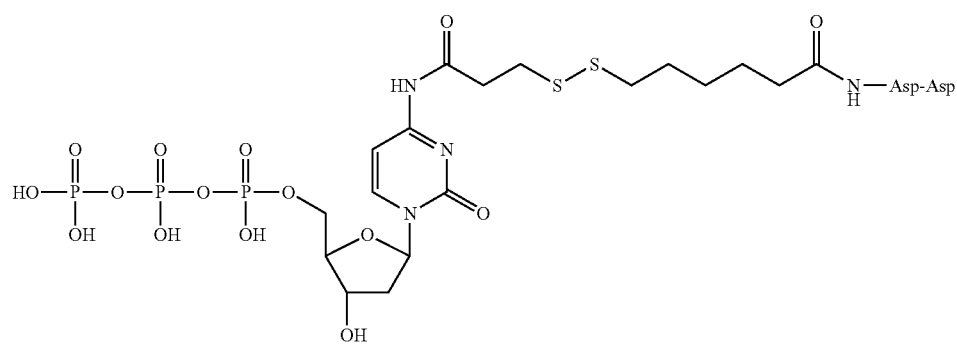
Scheme 1B
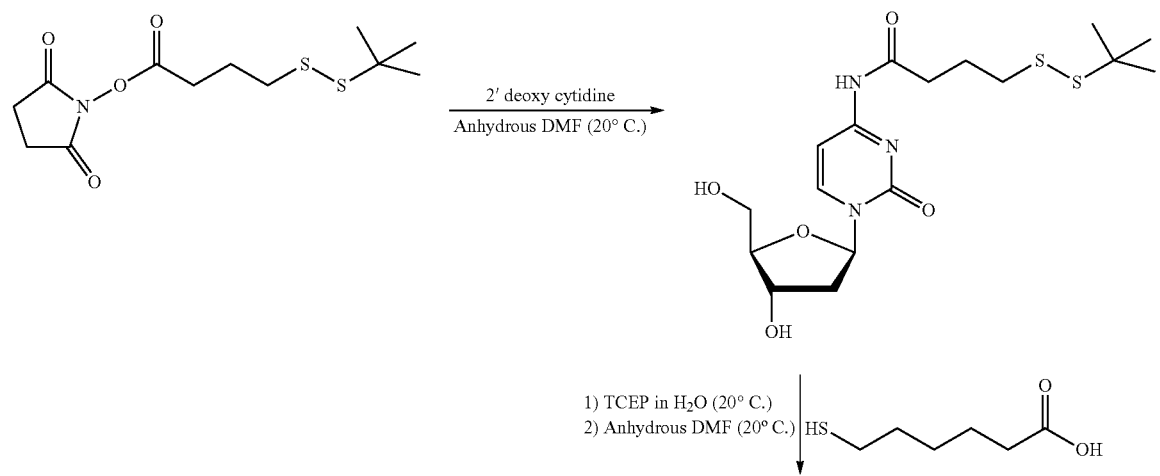
2' deoxy cytidine
Anhydrous DMF (20° C.)
1) TCEP in H₂O (20° C.)
2) Anhydrous DMF (20° C.)

-continued

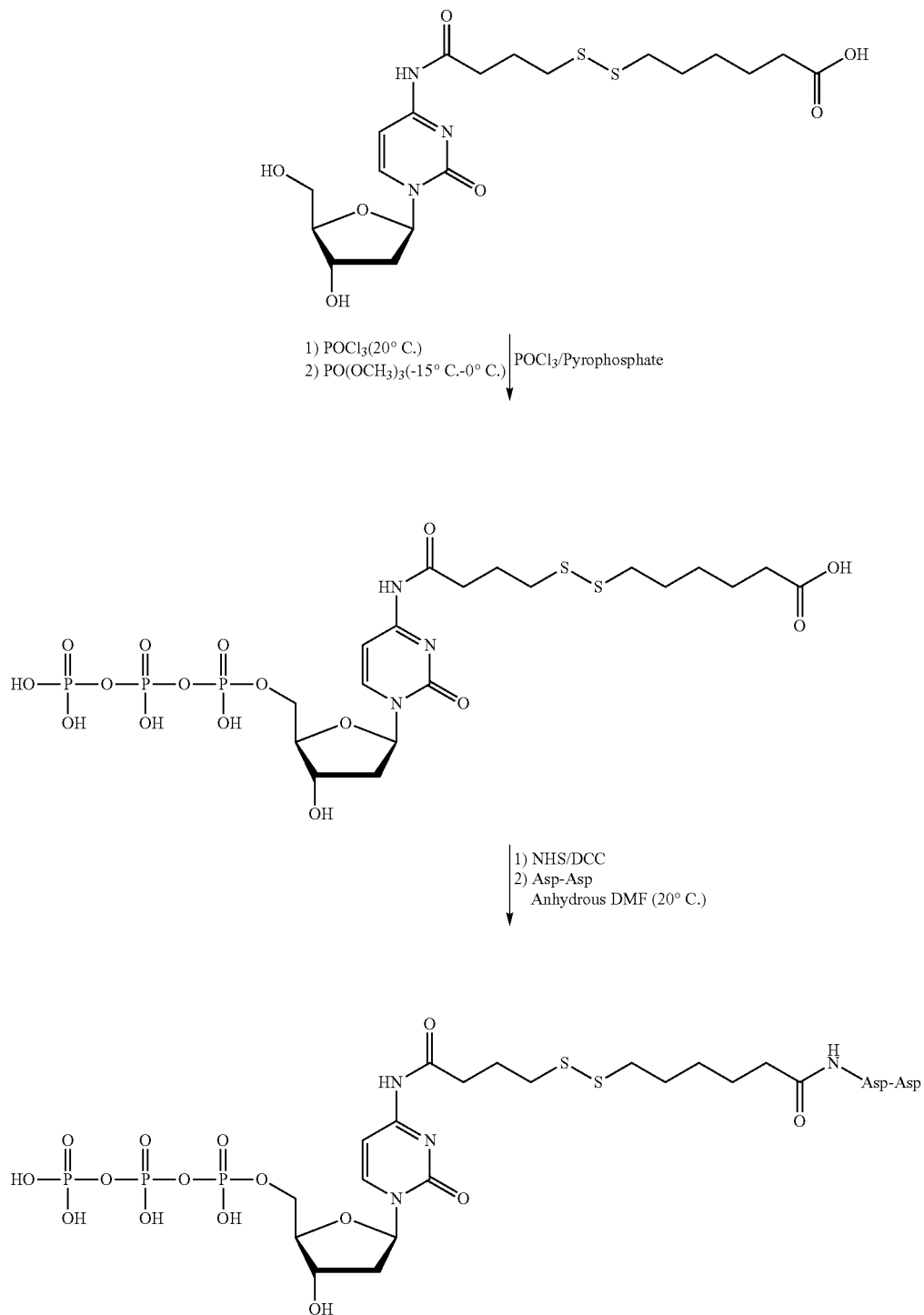

Figure 2A:
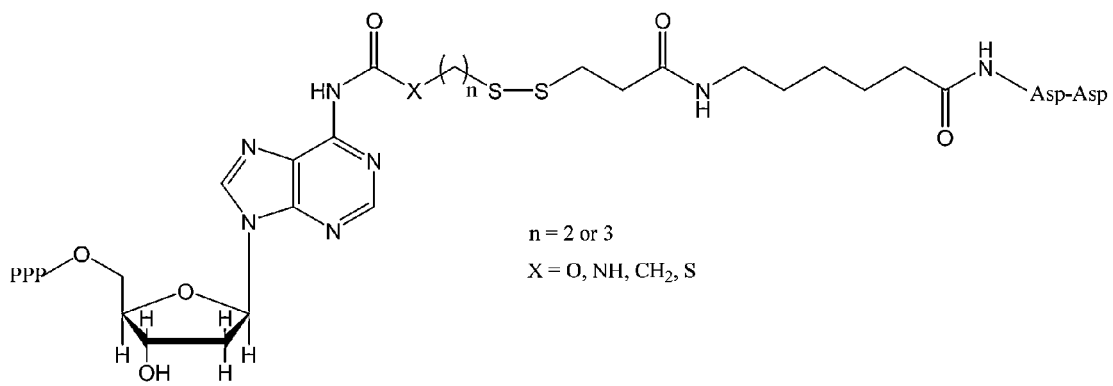
FIG. 2A shows a genus of deoxyadenosine triphosphate (dATP) analogs having a cleavable terminator linked at the N-6 position.
Figure 2B:
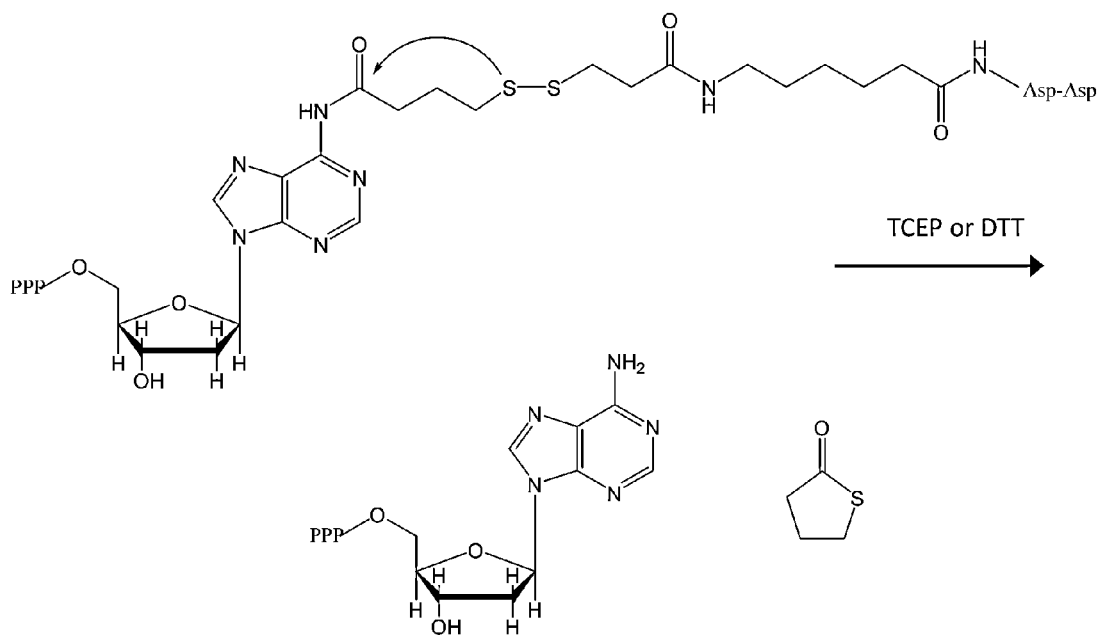
FIG. 2B shows cleavage of the cleavable terminator from a dATP analog of FIG. 2A to achieve a "natural" dATP and a cyclic leaving molecule.
Figure 3A:
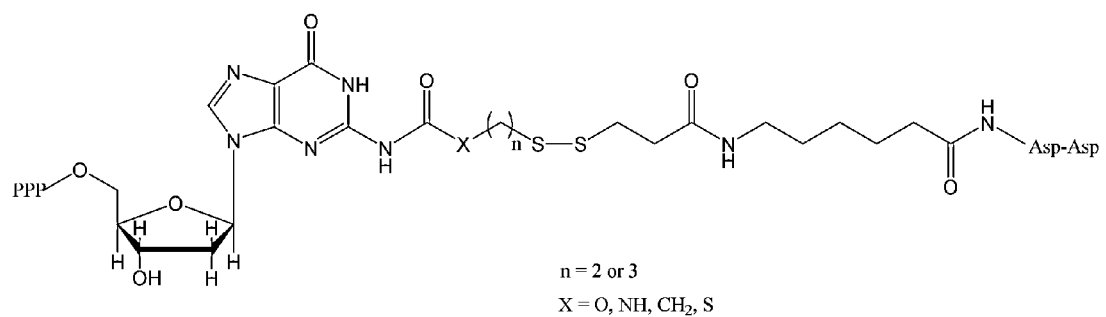
FIG. 3A shows a genus of deoxyguanosine triphosphate (dGTP) analogs having a cleavable terminator linked at the N-2 position.
Figure 3B:
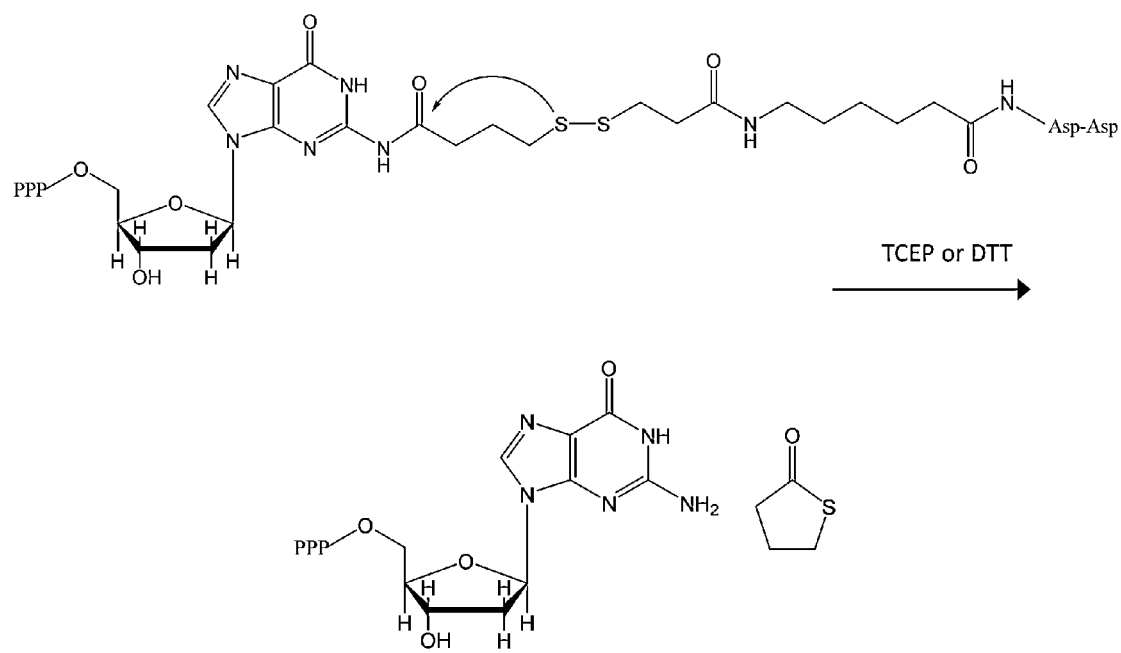
FIG. 3B shows cleavage of the cleavable terminator from a dGTP analog of FIG. 3A to achieve a "natural" dGTP and a cyclic leaving molecule.
Figure 4A:
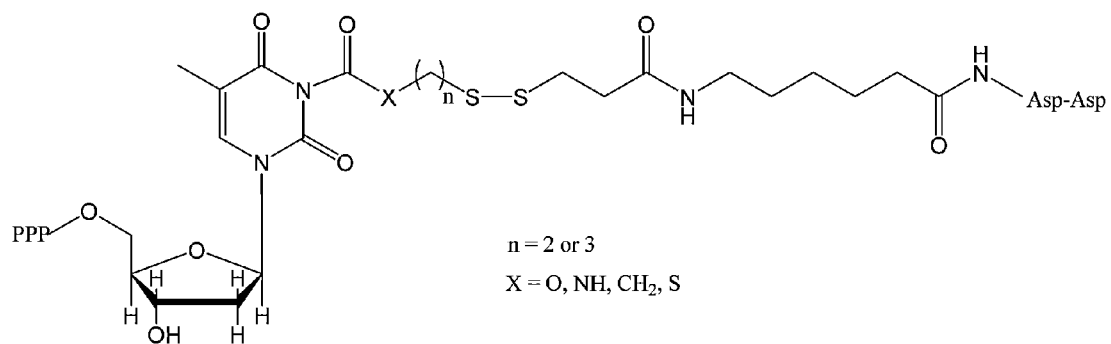
FIG. 4A shows a genus of deoxythymidine triphosphate (dTTP) analogs having a cleavable terminator linked at the N-3 position.
Figure 4B:
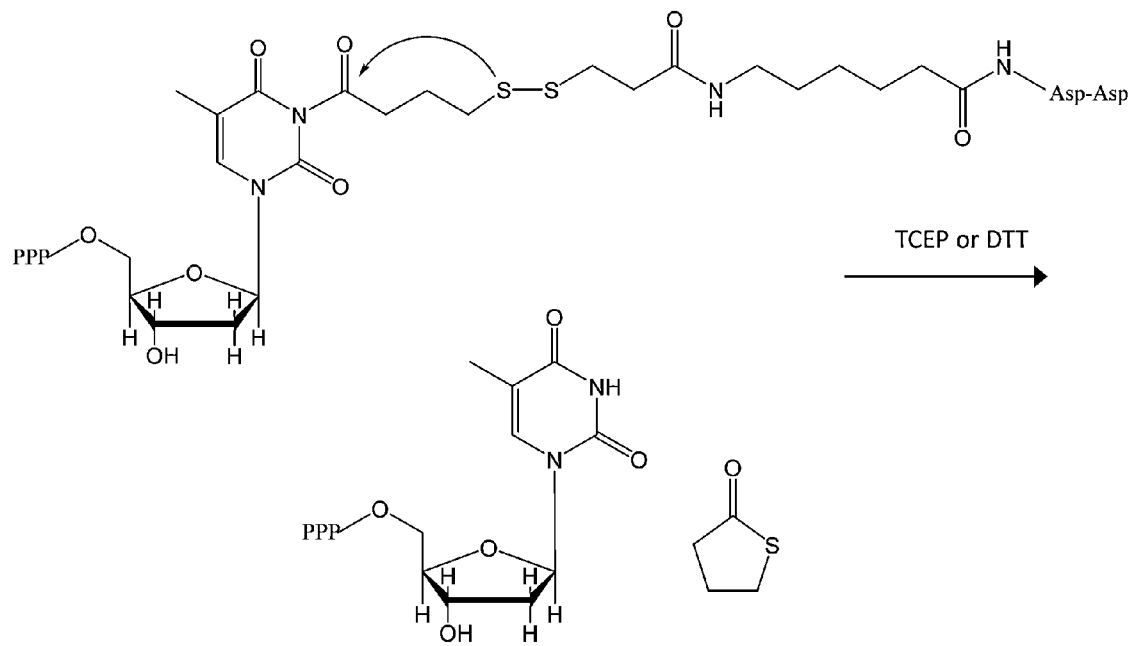
FIG. 4B shows cleavage of the cleavable terminator from a dTTP analog of FIG. 4A to achieve a "natural" dTTP and a cyclic leaving molecule.
Figure 5A:
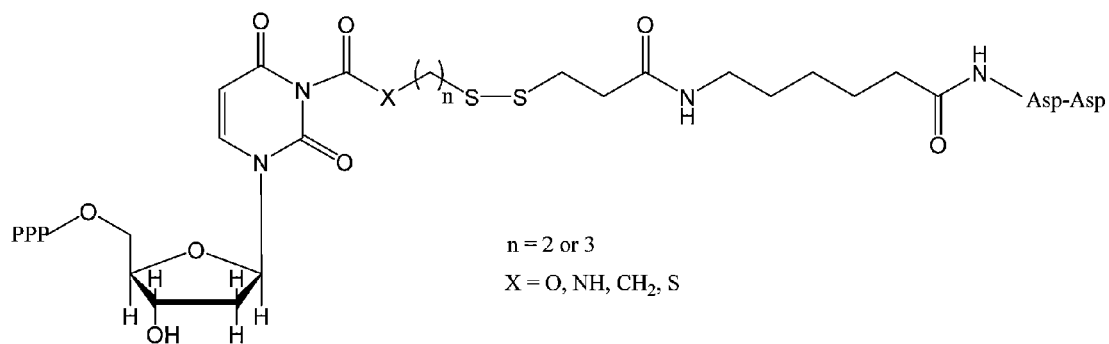
FIG. 5A shows a genus of deoxyuridine triphosphate (dUTP) analogs having a cleavable terminator linked at the N-3 position.
Figure 5B:
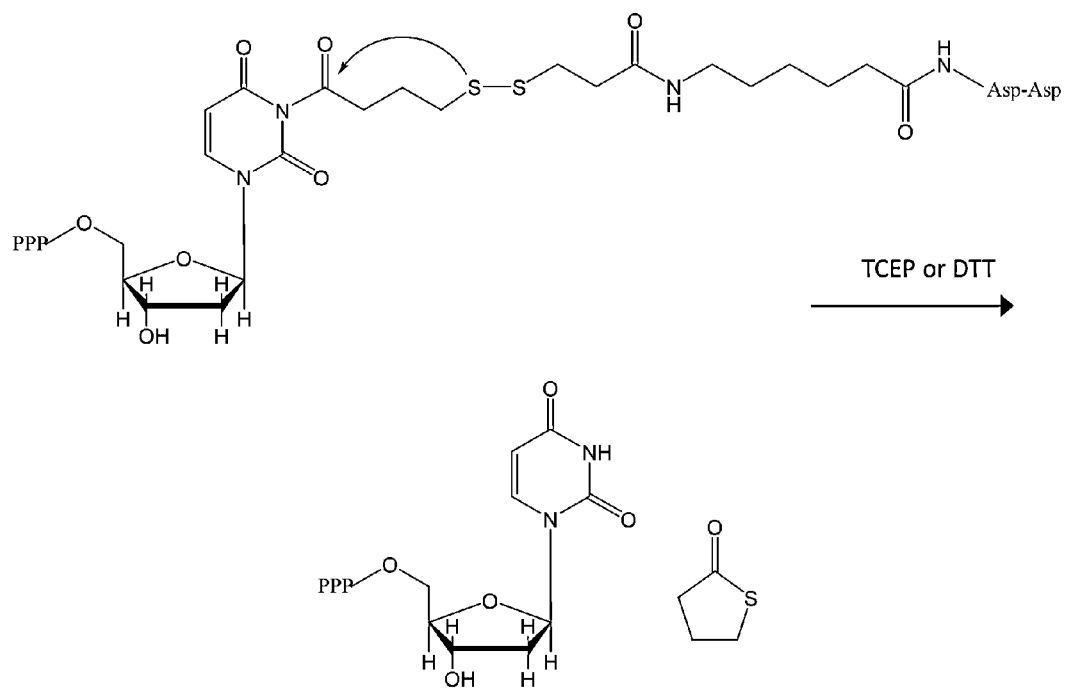
FIG. 5B shows cleavage of the cleavable terminator from a dUTP analog of FIG. 5A to achieve a dUTP and a cyclic leaving molecule.

In a fashion analogous to Schemes 1A and 1B, nucleotide analogs of the type NTP-linker-inhibitor can also be formed by attaching the linker-inhibitor moiety to the N6 of adenine (FIG. 2), the N2 of guanine (FIG. 3), the N3 of thymine (FIG. 4), or the N3 of uracil (FIG. 5), thereby providing analogs of the "naturally-occurring" dNTPs, as well as a deoxyuracil nucleotide (dUTP). While it is unlikely that there will be wide use of a dUTP, the synthesis is straightforward based upon the chemistry.

The invention is not limited to the linking chemistry of Schemes 1A and 1B, however, as carbamate, amide, or other self-eliminating linkages could also be employed. For example, nucleotides can also be prepared with Staudinger linkers, as shown in Scheme 2.

analog undergoes cleavage under aqueous conditions with the addition of azide and triphenylphosphine. The Staudinger

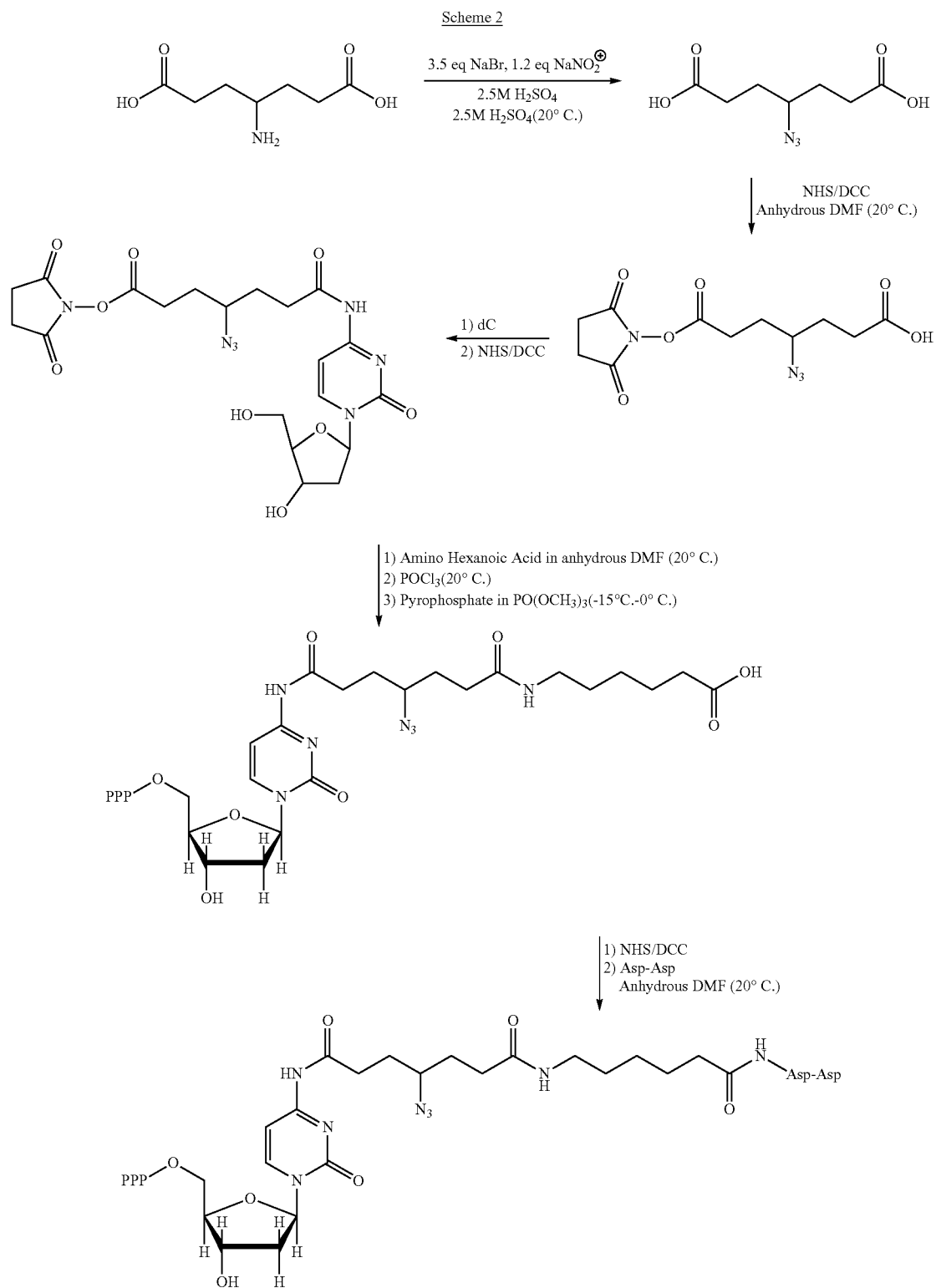

Figure 6:
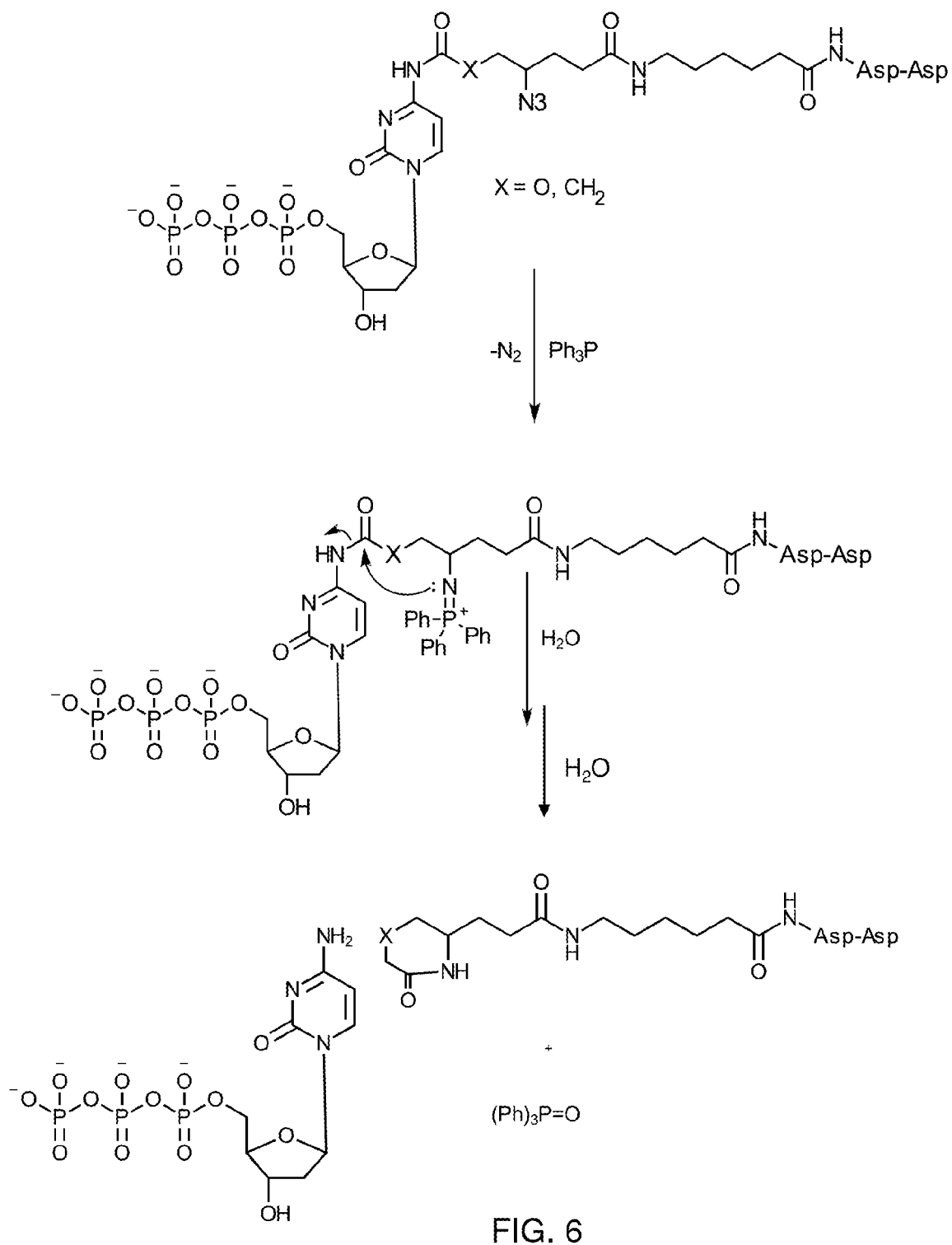
FIG. 6 shows an exemplary deoxycytidine triphosphate (dCTP) analog having a Staudinger linker connecting a blocking Asp-Asp molecule to the N-4 position of the deoxycytidine and subsequent cleavage of the Staudinger linker under aqueous conditions to achieve a dCTP and a leaving group.

A deoxycytidine triphosphate (dCTP) analog created with a Staudinger linker (Scheme 2) to an Asp-Asp blocking group is shown in FIG. 6. As shown in FIG. 6, the Staudinger dCTP analog shown in FIG. 6 is also suitable for nucleotide extension using nucleotidyl transferases, such as TdT, as described above and exemplified in FIGS. 1-5. While not shown explicitly in the FIGS., one of skill in the art can use Scheme 2 in conjunction with the suitable reactant to produce other nucleotide analogs having Staudinger linkers as needed for complete de novo nucleotide synthesis. In a fashion analogous to FIG. 6, nucleotide analogs of Scheme 2 can be formed by attaching the Staudinger moiety to the N6 of adenine, the N2 of guanine, the N3 of thymine, or the N3 of uracil, thereby providing analogs of the "naturally-occurring" dNTPs, as well as a deoxyuracil nucleotide (dUTP).

Figure 12:
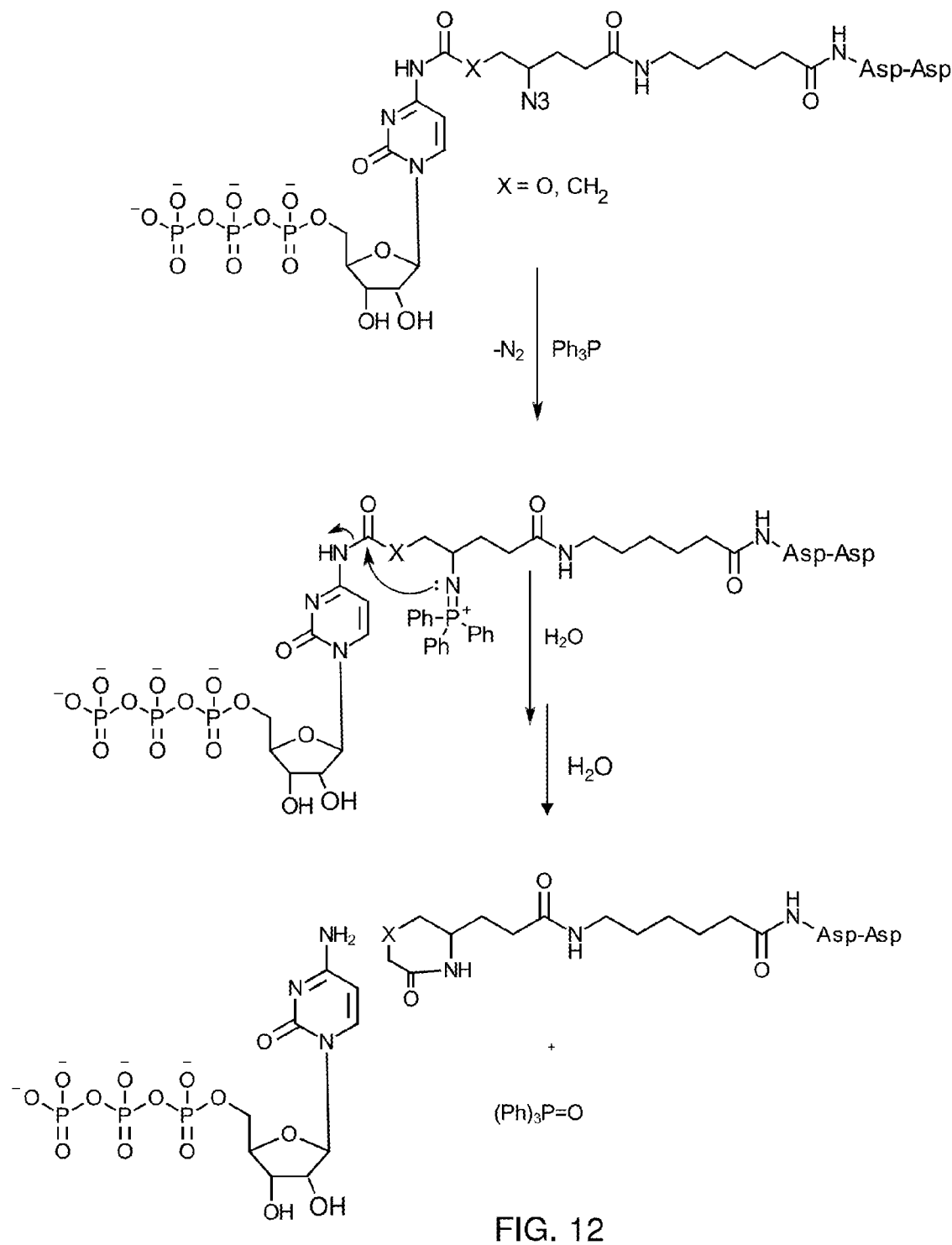
FIG. 12 shows an exemplary cytidine triphosphate (rCTP) analog having a Staudinger linker connecting a blocking Asp-Asp molecule to the N-4 position of the cytidine and subsequent cleavage of the Staudinger linker under aqueous conditions to achieve a rCTP and a leaving group.

The methodologies of Scheme 1A can be used to produce corresponding ribonucleotide analogs, e.g., as shown in FIGS. 7-10, by starting with the appropriate ribonucleotide reactants. Ribonucleotide analogs comprising the Staudinger linker can also be created using Scheme 2 in order to form the needed ribonucleotide analogs, including, e.g., CTP analogs, as shown in FIG. 12. Furthermore, all of the ribonucleotide analogs, i.e., C, A, T, G, U, can be formed using a reaction similar to Scheme 2.

Enzymes

The methods of the invention employ nucleotidyl transferases to assemble the nucleotide analogs into polynucleotides. Nucleotidyl transferases include several families of related transferase and polymerase enzymes. Some nucleotidyl transferases polymerize deoxyribonucleotides more efficiently than ribonucleotides, some nucleotidyl transferases polymerize ribonucleotides more efficiently than deoxyribonucleotides, and some nucleotidyl transferases polymerize ribonucleotides and deoxyribonucleotides at approximately the same rate.

Of particular import to the invention, transferases having polymerase activity, such as terminal deoxynucleotidyl transferase (TdT), are capable of catalyzing the addition of deoxyribonucleotides to the 3' end of a nucleotide chain, thereby increasing chain length in DNA nucleotides. TdT will only catalyze the addition of 1-2 ribonucleotides to the growing end of a DNA strand which could be useful in the construction of site specific DNA-RNA chimeric polynucleotides. In particular, calf thymus TdT, sourced from engineered *E. coli*, is suitable for use with the invention and available from commercial sources such as Thermo Scientific (Pittsburgh, Pa.). The amino acid sequence corresponding to calf TdT is listed in Table 1 as SEQ ID NO. 1.

TABLE 1

| Amino Acid Sequence of Bovine TdT |
|---|
| SEQ ID NO. 1: |
| MAQQRQHQRL PMDPLCTASS GPRKKRPRQV GASMASPPHD |
| IKFQNLVLFI LEKKMGTTRR NFLMELARRK GFRVENELSD |
| SVTHIVAENN SGSEVLEWLQ VQNIRASSQL ELLDVSWLIE |
| SMGAGKPVEI TGKHQLVVRT DYSATPNPGF QKTPPLAVKK |
| ISQYACQRKT TLNNYNHIFT DAFEILAENS EFKENEVSYV |
| TFMRAASVLK SLPFTIISMK DTEGIPCLGD KVKCIIEEII |
| EDGESSEVKA VLNDERYQSF KLFTSVFGVG LKTSEKWFRM |
| GFRSLSKIMS DKTLKFTKMQ KAGFLYYEDL VSCVTRAEAE |
| AVGVLVKEAV WAFLPDAFVT MTGGFRRGKK IGHDVDFLIT |
| SPGSAEDEEQ LLPKVINLWE KKGLLLYYDL VESTFEKFKL |
| PSRQVDTLDH FQKCFLILKL HHQRVDSSKS NQQEGKTWKA |
| IRVDLVMCPY ENRAFALLGW TGSRQFERDI RRYATHERKM |
| MLDNHALYDK TKRVFLKAES EEEIFAHLGL DYIEPWERNA |

The nucleotide sequence corresponding to calf TdT is listed in Table 2 as SEQ ID NO. 2.

TABLE 2

| Nucleic Acid Sequence of Bovine TdT |
|---|
| SEQ ID NO. 2: |
| ctcttctgga gataccactt gatggcacag cagaggcagc |
| atcagcgtct tcccatggat ccgctgtgca cagcctcctc |
| aggccctcgg aagaagagac ccaggcaggt gggtgcctca |
| atggcctccc ctcctcatga catcaagttt caaaatttgg |
| tcctcttcat tttggagaag aaaatgggaa ccacccgcag |
| aaacttcctc atggagctgg ctcgaaggaa aggtttcagg |
| gttgaaaatg agctcagtga ttctgtcacc cacattgtag |
| cagaaaacaa ctctggttca gaggttctcg agtggcttca |
| ggtacagaac ataagagcca gctcgcagct agaactcctt |
| gatgtctcct ggctgatcga aagtatggga gcaggaaaac |
| cagtggagat tacaggaaaa caccagcttg ttgtgagaac |
| agactattca gctaccccaa acccaggctt ccagaagact |
| ccaccacttg ctgtaaaaaa gatctcccag tacgcgtgtc |
| aaagaaaaac cactttgaac aactataacc acatattcac |
| ggatgccttt gagatactgg ctgaaaattc tgagtttaaa |
| gaaaatgaag tctcttatgt gacatttatg agagcagctt |
| ctgtacttaa atctctgcca ttcacaatca tcagtatgaa |
| ggatacagaa ggaattccct gcctggggga caaggtgaag |
| tgtatcatag aggaaattat tgaagatgga gaaagttctg |
| aagttaaagc tgtgttaaat gatgaacgat atcagtcctt |
| caaactcttt acttctgttt ttggagtggg actgaagaca |
| tctgagaaat ggttcaggat ggggttcaga tctctgagta |
| aaataatgtc agacaaaacc ctgaaattca caaaaatgca |
| gaaagcagga tttctctatt atgaagacct tgtcagctgc |
| gtgaccaggg ccgaagcaga ggcggttggc gtgctggtta |
| aagaggctgt gtgggcattt ctgccggatg cctttgtcac |
| catgacagga ggattccgca ggggtaagaa gattgggcat |
| gatgtagatt ttttaattac cagcccagga tcagcagagg |
| atgaagagca acttttgcct aaagtgataa acttatggga |
| aaaaaaggga ttactttat attatgacct tgtggagtca |
| acatttgaaa agttcaagtt gccaagcagg caggtggata |
| ctttagatca ttttcaaaaa tgctttctga ttttaaaatt |
| gcaccatcag agagtagaca gtagcaagtc caaccagcag |
| gaaggaaaga cctggaaggc catccgtgtg gacctggtta |
| tgtgcccta cgagaaccgt gcctttgccc tgctaggctg |
| gactggctcc cggcagtttg agagagacat ccggcgctat |
| gccacacacg agcggaagat gatgctggat aaccacgctt |

TABLE 2-continued

Nucleic Acid Sequence of Bovine TdT

```
tatatgacaa gaccaagagg gtatttctca aagcggaaag tgaagaagaa atctttgcac atctgggatt ggactacatt gaaccatggg aaagaaatgc ttaggagaaa gctgtcaact tttttctttt ctgttctttt tttcaggtta gacaaattat gcttcatatt ataatgaaag atgccttagt caagtttggg attctttaca ttttaccaag atgtagattg cttctagaaa taagtagttt tggaaacgtg atcaggcacc ccctgggtta tgctctggca agccatttgc aggactgatg tgtagaactc gcaatgcatt ttccatagaa acagtgttgg aattggtggc tcatttccag ggaagttcat caaagcccac tttgcccaca gtgtagctga aatactgtat acttgccaat aaaaatagga aac
```

While commercially-available TdT is suitable for use with the methods of the invention, modified TdT, e.g., having an amino acid sequence at least 95% in common with SEQ ID NO. 1, e.g., having an amino acid sequence at least 98% in common with SEQ ID NO. 1, e.g., having an amino acid sequence at least 99% in common with SEQ ID NO. 1, may be used with the methods of the invention. An organism that expresses a suitable nucleotidyl transferase may comprise a nucleic acid sequence at least 95% in common with SEQ ID NO. 2, e.g., at least 98% in common with SEQ ID NO. 2, e.g., at least 99% in common with SEQ ID NO. 2. In some instances, a modified TdT will result in more efficient generation of polynucleotides, or allow better control of chain length. Other modifications to the TdT may change the release characteristics of the enzyme, thereby reducing the need for aqueous reducing agents such as TCEP or DTT.

For the synthesis of RNA polynucleotides, a nucleotidyl transferase like E. coli poly(A) polymerase can be used to catalyze the addition of ribonucleotides to the 3' end of a ribonucleotide initiator. In other embodiments, E. coli poly (U) polymerase may be more suitable for use with the methods of the invention. Both E. coli poly(A) polymerase and E. coli poly(U) polymerase are available from New England Biolabs (Ipswich, Mass.). These enzymes may be used with 3'unblocked reversible terminator ribonucleotide triphosphates (rNTPs) to synthesize RNA. In certain embodiments, RNA may be synthesized using 3'blocked, 2'blocked, or 2'-3'blocked rNTPs and poly(U) polymerase or poly(A) polymerase. The amino acid and nucleotide sequences for E. coli Poly(A) polymerase and E. coli Poly(U) polymerase are reproduced below. Modified E. coli Poly(A) polymerase or E. coli Poly(U) polymerase may be suitable for use with the methods of the invention. For example, an enzyme, having an amino acid sequence at least 95% in common with SEQ ID NO. 3, e.g., having an amino acid sequence at least 98% in common with SEQ ID NO. 3, e.g., having an amino acid sequence at least 99% in common with SEQ ID NO. 3, may be used with the methods of the invention. An organism that expresses a suitable enzyme may comprise a nucleic acid sequence at least 95% in common with SEQ ID NO. 4, e.g., at least 98% in common with SEQ ID NO. 4, e.g., at least 99% in common with SEQ ID NO. 4. Alternatively, an enzyme having an amino acid sequence at least 95% in common with SEQ ID NO. 5, e.g., having an amino acid sequence at least 98% in common with SEQ ID NO. 5, e.g., having an amino acid sequence at least 99% in common with SEQ ID NO. 5, may be used with the methods of the invention. An organism that expresses a suitable enzyme may comprise a nucleic acid sequence at least 95% in common with SEQ ID NO. 6, e.g., at least 98% in common with SEQ ID NO. 6, e.g., at least 99% in common with SEQ ID NO. 6.

TABLE 3

Amino Acid Sequence of E. coli Poly(A) polymerase

```
SEQ ID NO. 3:
MFTRVANFCR KVLSREESEA EQAVARPQVT VIPREQHAIS

RKDISENALK VMYRLNKAGY EAWLVGGGVR DLLLGKKPKD

FDVTTNATPE QVRKLFRNCR LVGRRFRLAH VMFGPEIIEV

ATFRGHHEGN VSDRTTSQRG QNGMLLRDNI FGSIEEDAQR

RDFTINSLYY SVADFTVRDY VGGMKDLKDG VIRLIGNPET

RYREDPVRML RAVRFAAKLG MRISPETAEP IPRLATLLND

IPPARLFEES LKLLQAGYGY ETYKLLCEYH LFQPLFPTIT

RYFTENGDSP MERIIEQVLK NTDTRIHNDM RVNPAFLFAA

MFWYPLLETA QKIAQESGLT YHDAFALAMN DVLDEACRSL

AIPKRLTTLT RDIWQLQLRM SRRQGKRAWK LLEHPKFRAA

YDLLALRAEV ERNAELQRLV KWWGEFQVSA PPDQKGMLNE

LDEEPSPRRR TRRPRKRAPR REGTA
```

The nucleotide sequence corresponding to E. coli poly(A) polymerase is listed in Table 4 as SEQ ID NO. 4.

TABLE 4

Nucleotide Sequence of E. coli Poly(A) polymerase

```
SEQ ID NO. 4:
atttttaccc gagtcgctaa tttttgccgc aaggtgctaa gccgcgagga aagcgaggct gaacaggcag tcgcccgtcc acaggtgacg gtgatcccgc gtgagcagca tgctatttcc cgcaaagata tcagtgaaaa tgccctgaag gtaatgtaca ggctcaataa agcgggatac gaagcctggc tggttggcgg cggcgtgcgc gacctgttac ttggcaaaaa gccgaaagat tttgacgtaa ccactaacgc cacgcctgag caggtgcgca aactgttccg taactgccgc ctggtgggtc gccgtttccg tctggctcat gtaatgtttg gcccggagat tatcgaagtt gcgaccttcc gtggacacca cgaaggtaac gtcagcgacc gcacgacctc ccaacgcggg caaaacggca tgttgctgcg cgacaacatt ttcggctcca tcgaagaaga cgcccagcgc cgcgatttca ctatcaacag cctgtattac agcgtagcgg attttaccgt ccgtgattac gttggcggca tgaaggatct gaaggacggc gttatccgtc tgattggtaa cccggaaacg cgctaccgtg aagatccggt acgtatgctg cgcgcgggtac
```

TABLE 4-continued

Nucleotide Sequence of E. coli Poly(A) polymerase gttttgccgc caaattgggt atgcgcatca gcccggaaac
cgcagaaccg atccctcgcc tcgctaccct gctgaacgat
atcccaccgg cacgcctgtt tgaagaatcg cttaaactgc
tacaagcggg ctacggttac gaaacctata agctgttgtg
tgaatatcat ctgttccagc cgctgttccc gaccattacc
cgctacttca cggaaaatgg cgacagcccg atggagcgga
tcattgaaca ggtgctgaag aataccgata cgcgtatcca
taacgatatg cgcgtgaacc cggcgttcct gtttgccgcc
atgttctggt acccactgct ggagacggca cagaagatcg
cccaggaaag cggcctgacc tatcacgacg ctttcgcgct
ggcgatgaac gacgtgctgg acgaagcctg ccgttcactg
gcaatcccga aacgtctgac gacattaacc cgcgatatct
ggcagttgca gttgcgtatg tcccgtcgtc agggtaaacg
cgcatggaaa ctgctggagc atcctaagtt ccgtgcggct
tatgacctgt tggccttgcg agctgaagtt gagcgtaacg
ctgaactgca gcgtctggtg aaatggtggg gtgagttcca
ggtttccgcg ccaccagacc aaaaagggat gctcaacgag
ctggatgaag aaccgtcacc gcgtcgtcgt actcgtcgtc
cacgcaaacg cgcaccacgt cgtgagggta ccgcatga

TABLE 5

Amino Acid Sequence of E. coli Poly(U) polymerase

SEQ ID NO. 5:
GSHMSYQKVP NSHKEFTKFC YEVYNEIKIS DKEFKEKRAA
LDTLRLCLKR ISPDAELVAF GSLESGLALK NSDMDLCVLM
DSRVQSDTIA LQFYEELIAE GFEGKFLQRA RIPIIKLTSD
TKNGFGASFQ CDIGFNNRLA IHNTLLLSSY TKLDARLKPM
VLLVKHWAKR KQINSPYFGT LSSYGYVLMV LYYLIHVIKP
PVFPNLLLSP LKQEKIVDGF DVGFDDKLED IPPSQNYSSL
GSLLHGFFRF YAYKFEPREK VVTFRRPDGY LTKQEKGWTS
ATEHTGSADQ IIKDRYILAI EDPFEISHNV GRTVSSSGLY
RIRGEFMAAS RLLNSRSYPI PYDSLFEEA

The nucleotide sequence corresponding to E. coli poly(U) polymerase is listed in Table 6 as SEQ ID NO. 6.

TABLE 6

Nucleotide Sequence of E. coli Poly(A) polymerase

SEQ ID NO. 6:
ggcagccata tgagctatca gaaagtgccg aacagccata
aagaatttac caaattttgc tatgaagtgt ataacgaaat
taaaattagc gataaagaat ttaaagaaaa acgcgcggcg
ctggataccc tgcgcctgtg cctgaaacgc attagcccgg
atgcggaact ggtggcgttt ggcagcctgg aaagcggcct
ggcgctgaaa aacagcgata tggatctgtg cgtgctgatg
gatagccgcg tgcagagcga taccattgcg ctgcagtttt
atgaagaact gattgcggaa ggcttgaag gcaaatttct
gcagcgcgcg cgcattccga ttattaaact gaccagcgat
accaaaaacg gctttggcgc gagctttcag tgcgatattg
gctttaacaa ccgcctggcg attcataaca ccctgctgct
gagcagctat accaaactgg atgcgcgcct gaaaccgatg TABLE 6-continued Nucleotide Sequence of E. coli Poly(A) polymerase gtgctgctgg tgaaacattg ggcgaaacgc aaacagatta
acagcccgta ttttggcacc ctgagcagct atggctatgt
gctgatggtg ctgtattatc tgattcatgt gattaaaccg
ccggtgtttc cgaacctgct gctgagcccg ctgaaacagg
aaaaaattgt ggatggcttt gatgtgggct ttgatgataa
actggaagat attccgccga gccagaacta tagcagcctg
ggcagcctgc tgcatggctt ttttcgcttt tatgcgtata
aatttgaacc gcgcgaaaaa gtggtgacct ttcgccgccc
ggatggctat ctgaccaaac aggaaaaagg ctggaccagc
gcgaccgaac ataccggcag cgcggatcag attattaaag
atcgctatat tctggcgatt gaagatccgt ttgaaattag
ccataacgtg ggccgcaccg tgagcagcag cggcctgtat
cgcattcgcg gcgaatttat ggcggcgagc cgcctgctga
acagccgcag ctatccgatt ccgtatgata gcctgtttga
agaagcg As discussed above, the inhibitor coupled to the nucleotide analog will cause the transferase, e.g., TdT, to not release from the polynucleotide or prevent other analogs from being incorporated into the growing chain. A charged moiety results in better inhibition, however, research suggests that the specific chemical nature of the inhibitor is not particularly important. For example, both phosphates and acidic peptides can be used to inhibit enzymatic activity. See, e.g., Bowers et al., Nature Methods, vol. 6, (2009) p. 593-95, and U.S. Pat. No. 8,071,755, both of which are incorporated herein by reference in their entireties. In some embodiments, the inhibitor will include single amino acids or dipeptides, like -(Asp)$_2$, however the size and charge on the moiety can be adjusted, as needed, based upon experimentally determined rates of first nucleotide incorporation and second nucleotide incorporation. That is, other embodiments may use more or different charged amino acids or other biocompatible charged molecule.

Other methods of nucleotide synthesis may be used to build de novo oligonucleotides in a template independent fashion using nucleotidyl transferases or modified nucleotidyl transferases. In one embodiment, the polymerase/transferase enzymes can be modified so that they cease nucleotide addition when they encounter a modification to the phosphate of a 3'-unmodified dNTP analog. This scheme would require a deblocking reagent/reaction that modifies the phosphate end of the nucleotide analog, which frees up the nascent strand for subsequent nucleotide incorporation. Preferred embodiments of this approach would use nucleotide analogs modified only at the phosphates (alpha, beta or gamma) although modifications of the purine/pyrimidine base of the nucleotide are allowed.

Another embodiment for using non-template dependent polymerase/transferase enzymes would be to using protein engineering or protein evolution to modify the enzyme to remain tightly bound and inactive to the nascent strand after each single nucleotide incorporation, thus preventing any subsequent incorporation until such time as the polymerase/transferase is released from the strand by use of a releasing reagent/condition. Such modifications would be selected to allow the use of natural unmodified dNTPs instead of reversible terminator dNTPs. Releasing reagents could be high salt buffers, denaturants, etc. Releasing conditions could be high temperature, agitation, etc. For instance, mutations to the Loop1 and SD1 regions of TdT have been shown to dramatically alter the activity from a template-independent activity to more of a template dependent activity. Specific mutations of interest include but are not limited to $\Delta_3$384/391/392, del loop1 (386→398), L398A, D339A, F401A, and Q402K403C404→E402R403S404. Other means of accomplishing the goal of a post-incorporation tight binding (i.e., single turnover) TdT enzyme could include mutations to the residues responsible for binding the three phosphates of the initiator strand including but not limited to K261, R432, and R454.

Another embodiment for using non-template dependent polymerase/transferase enzymes would be to use protein engineering or protein evolution to modify the enzyme to accept 3-blocked reversible terminators with high efficiency. Most naturally occurring polymerase/transferase enzymes will not incorporate 3'-blocked reversible terminators due to steric constraints in the active site of the enzyme. Modifying either single or several aa residues in the active site of the enzyme can allow the highly efficient incorporation of 3'-blocked reversible terminators into a support bound initiator in a process completely analogous to that described above. After incorporation, the 3'-reversible terminator is removed with a deblocking reagent/condition thus generating a completely natural (scarless) single strand molecule ready for subsequent controlled extension reactions. There are residues close to the 3'-OH of the incoming dNTP which explains the propensity of TdT for incorporating ribonucleotide triphosphates as readily as deoxyribonucleotide triphosphates; residues including but not limited to those between $\beta 1$ and $\beta 2$ especially R334, Loop1, and those between $\alpha 13$ and $\alpha 14$, especially R454, are likely targets for mutagenesis to accommodate the bulk of 3'-reversible terminator groups and allow their efficient incorporation. In certain embodiments additional amino acid changes may be required to compensate for these residue alterations made to accommodate a 3'-reversible terminator. Another embodiment for using template-dependent polymerases would be to use the either 3'blocked or 3'unblocked dNTP analogs with a plurality of primer-template pairs attached to a solid support where the template is a nucleic acid analog that supports polymerase mediated primer extension of any of the four bases as specified by the user.

Another embodiment for using non-template dependent polymerase/transferase enzymes can use protein engineering or protein evolution to modify the enzyme to optimize the use of each of the four different nucleotides or even different modified nucleotide analogs in an analog specific manner. Nucleotide specific or nucleotide analog specific enzyme variants could be engineered to possess desirable biochemical attributes like reduced $K_m$ or enhanced addition rate which would further reduce the cost of the synthesis of desired polynucleotides.

Solid State Synthesis

Figure 7A:
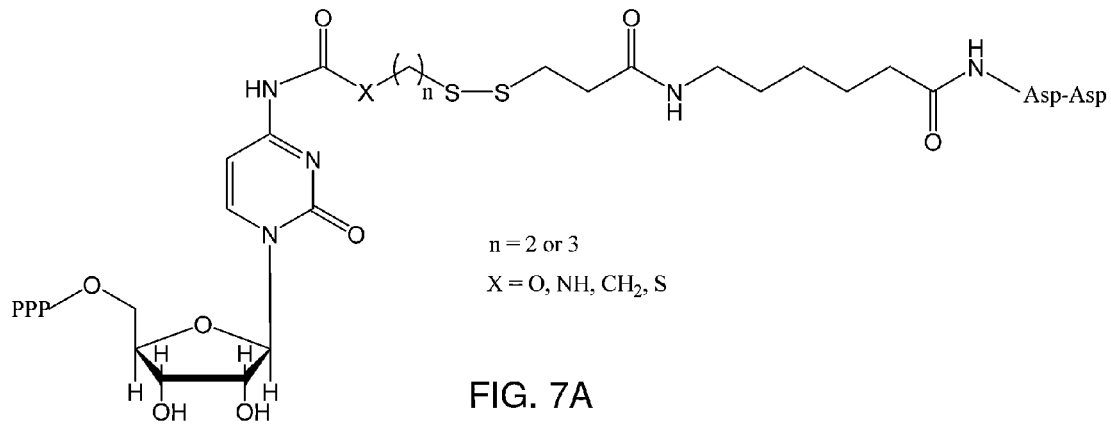
FIG. 7A shows a genus of cytidine triphosphate (rCTP) analogs having a cleavable terminator linked at the N-4 position.
Figure 7B:
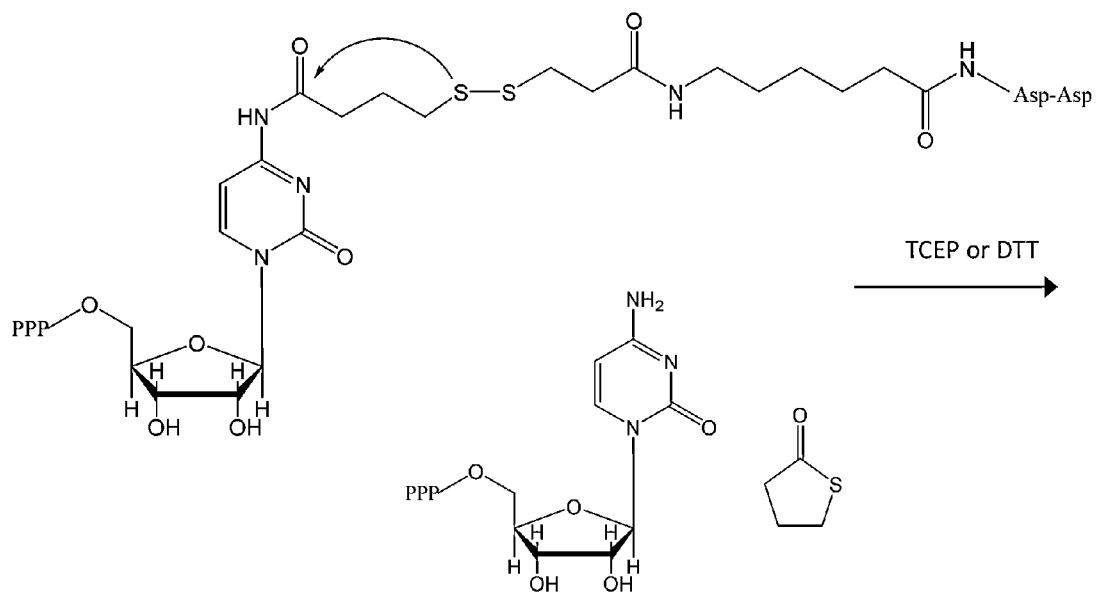
FIG. 7B shows cleavage of the cleavable terminator from a rCTP analog of FIG. 7A to achieve a "natural" rCTP and a cyclic leaving molecule.
Figure 8A:
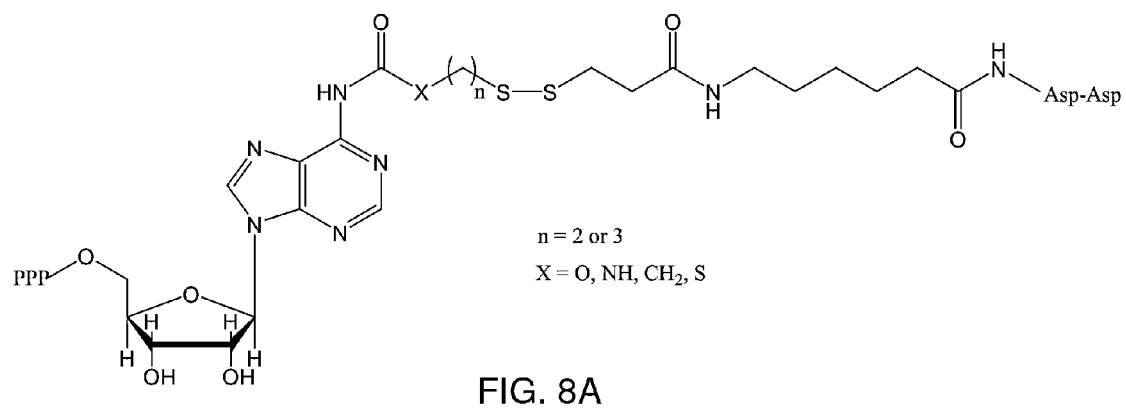
FIG. 8A shows a genus of adenosine triphosphate (rATP) analogs having a cleavable terminator linked at the N-6 position.
Figure 8B:
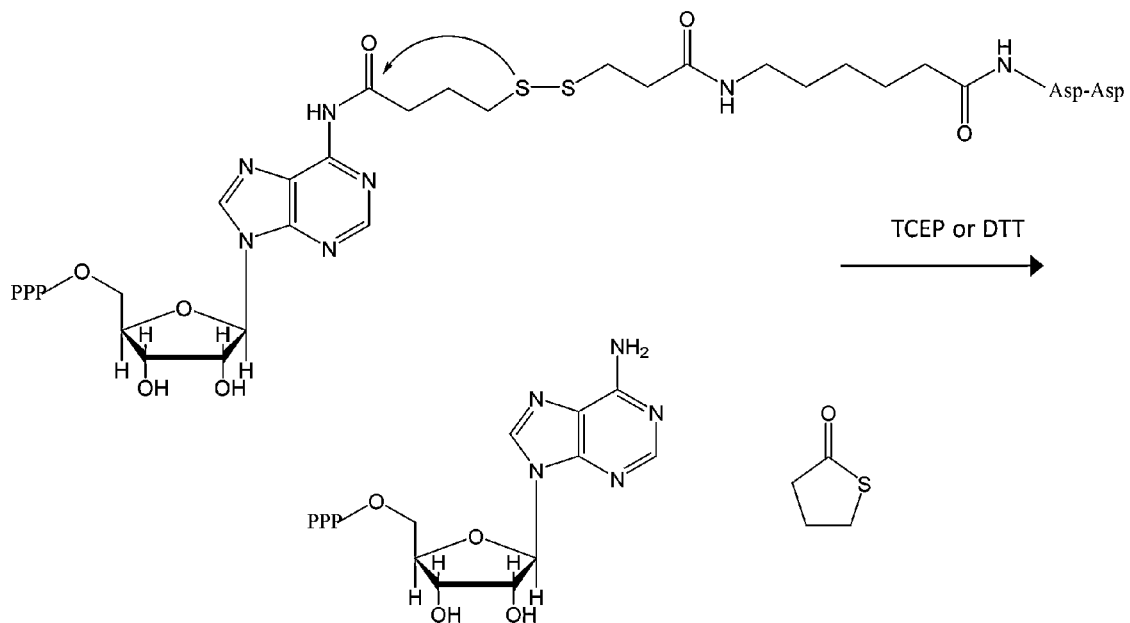
FIG. 8B shows cleavage of the cleavable terminator from an rATP analog of FIG. 8A to achieve a "natural" rATP and a cyclic leaving molecule.
Figure 9A:
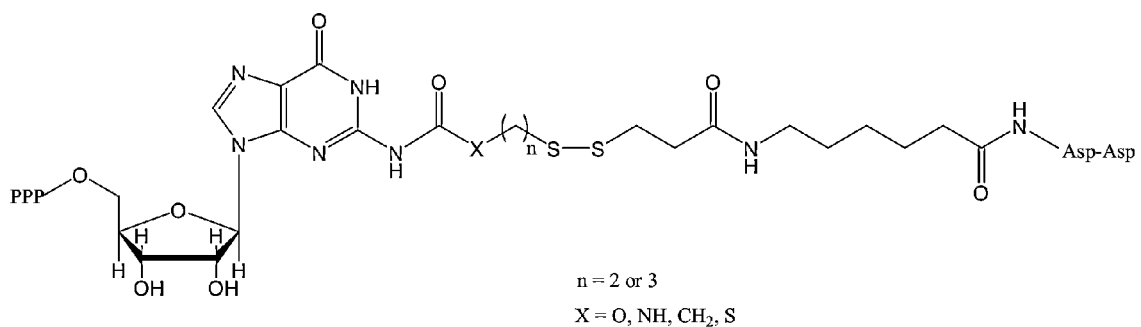
FIG. 9A shows n genus of guanosine triphosphate (rGTP) analogs having a cleavable terminator linked at the N-2 position.
Figure 9B:
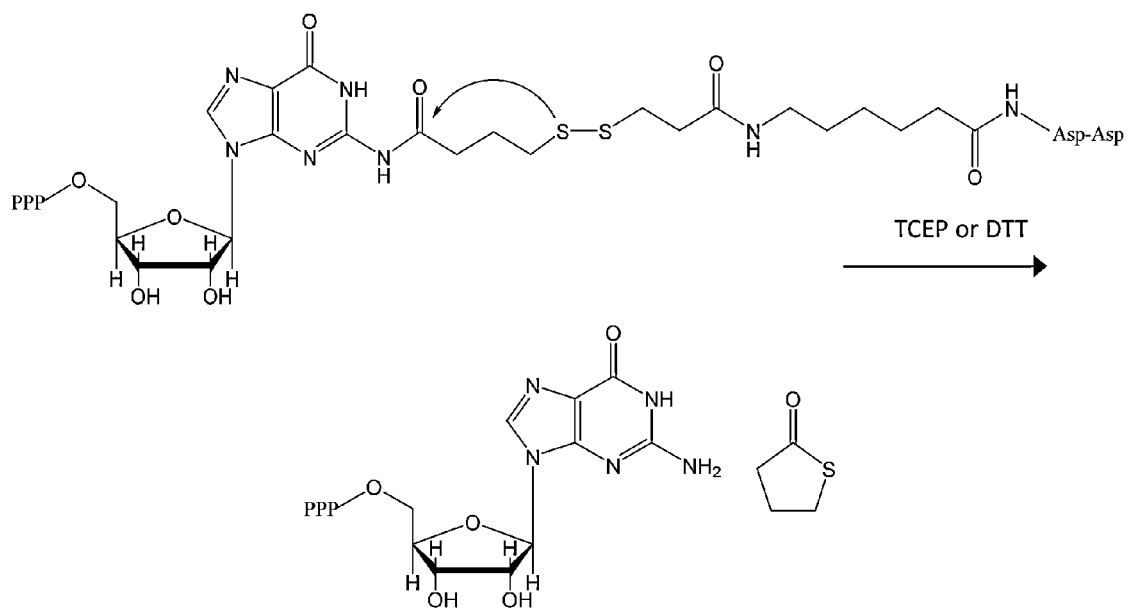
FIG. 9B shows cleavage of the cleavable terminator from a rGTP analog of FIG. 9A to achieve a "natural" rGTP and a cyclic leaving molecule.
Figure 10A:
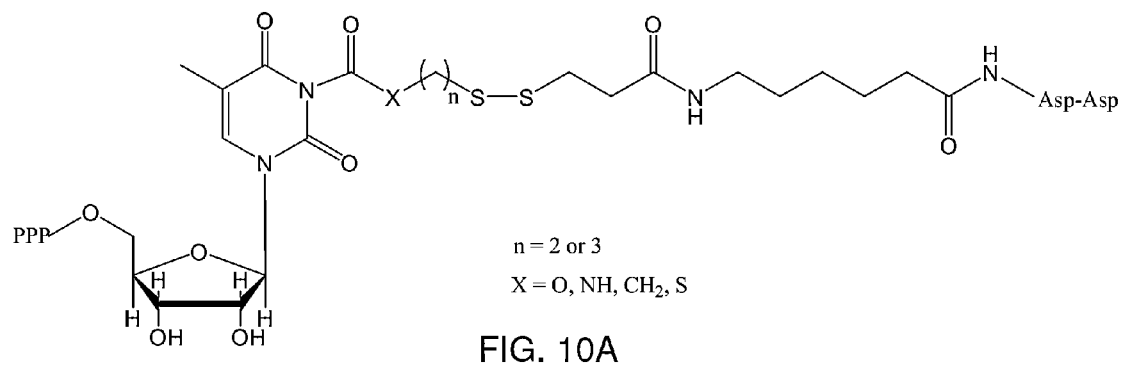
FIG. 10A shows a genus of thymidine triphosphate (rTTP) analogs having a cleavable terminator linked at the N-3 position.
Figure 10B:
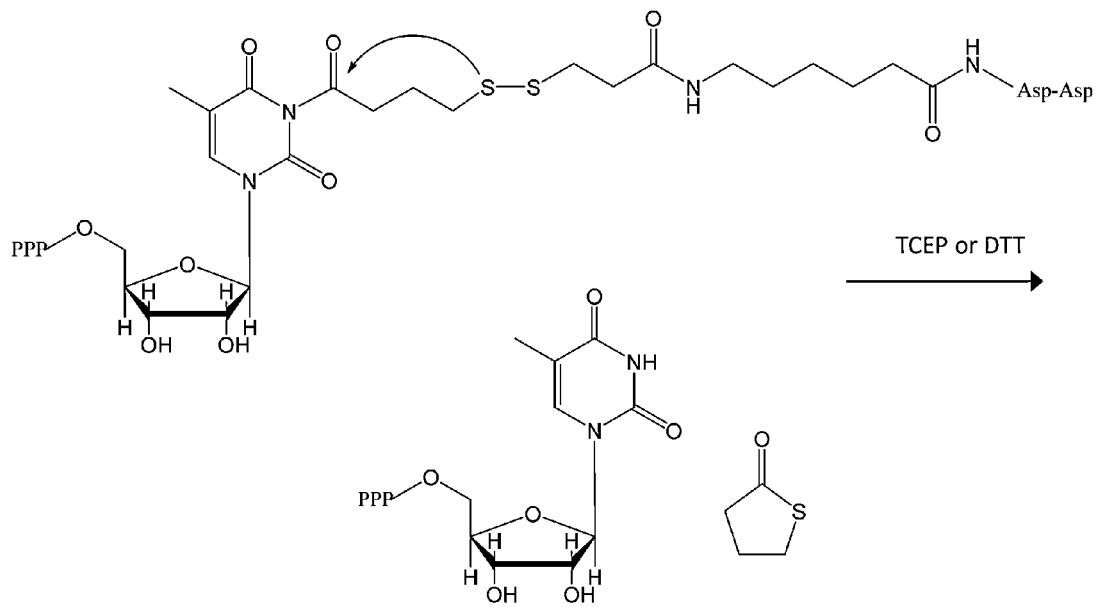
FIG. 10B shows cleavage of the cleavable terminator from a rTTP analog of FIG. 10A to achieve a "natural" rTTP and a cyclic leaving molecule.
Figure 11A:
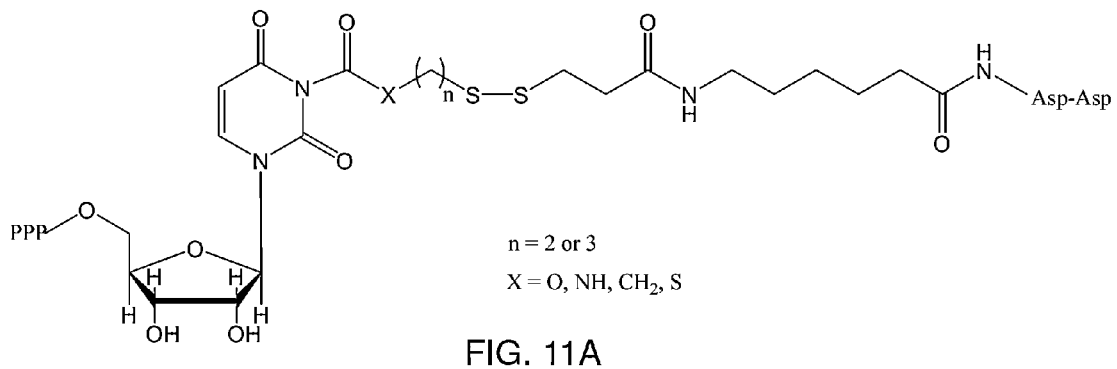
FIG. 11A shows a genus of uridine triphosphate (rUTP) analogs having a cleavable terminator linked at the N-3 position.
Figure 11B:
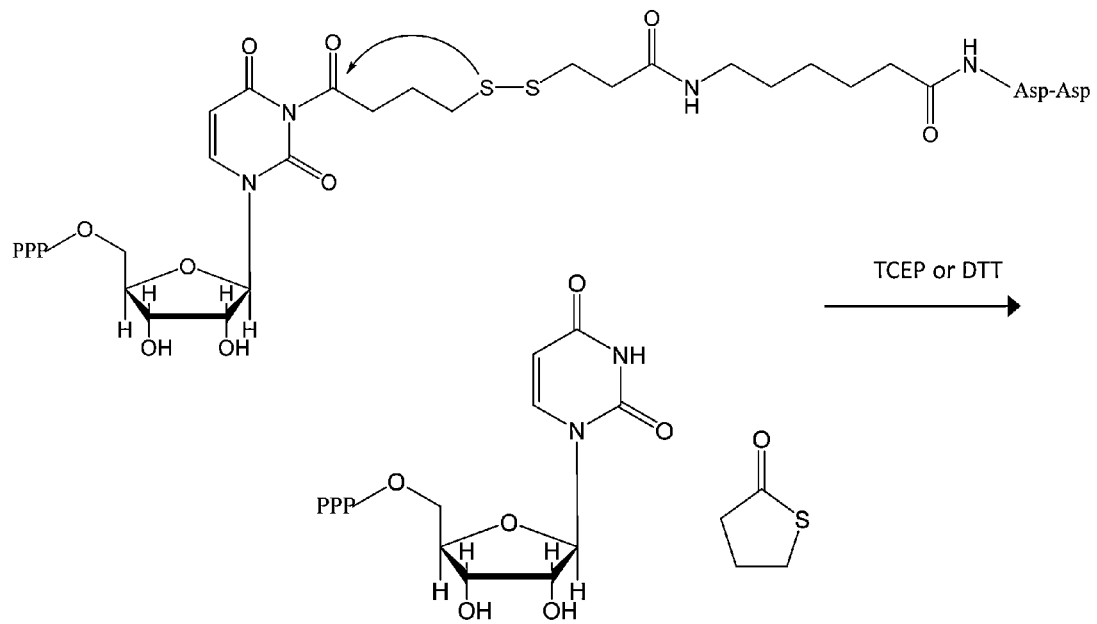
FIG. 11B shows cleavage of the cleavable terminator from a rUTP analog of FIG. 11A to achieve a rUTP and a cyclic leaving molecule.
Figure 13:
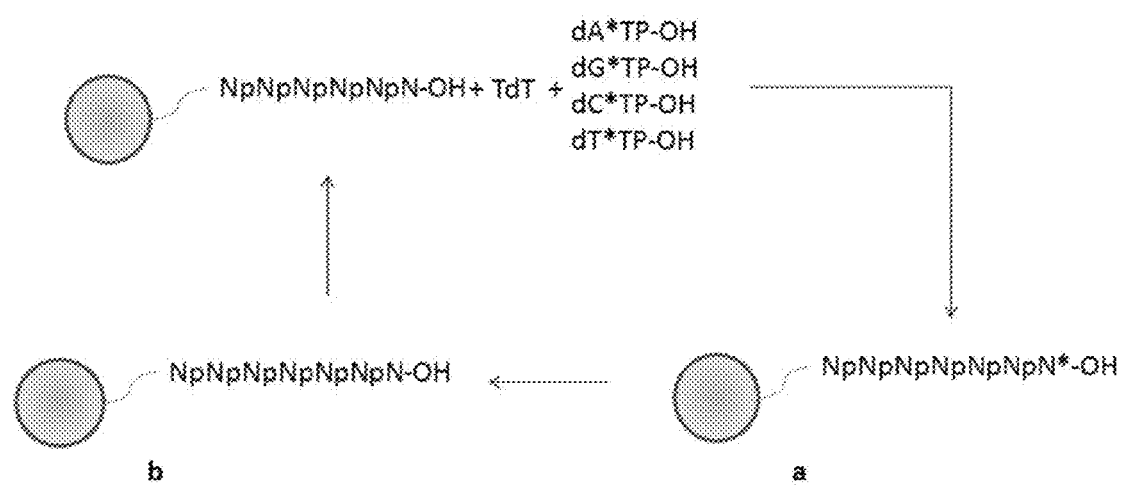
FIG. 13 shows an exemplary terminal deoxynucleotidyl transferase (TdT) mediated polynucleotide synthetic cycle, including: (a) incorporation of a nucleotide triphosphate analog comprising cleavable terminator, dN*TP-OH, and (b) removal of the terminating blocking group (indicated by *), thus enabling the next dN*TP-OH to be incorporated, wherein N=A, G, C, or T.
Figure 14:
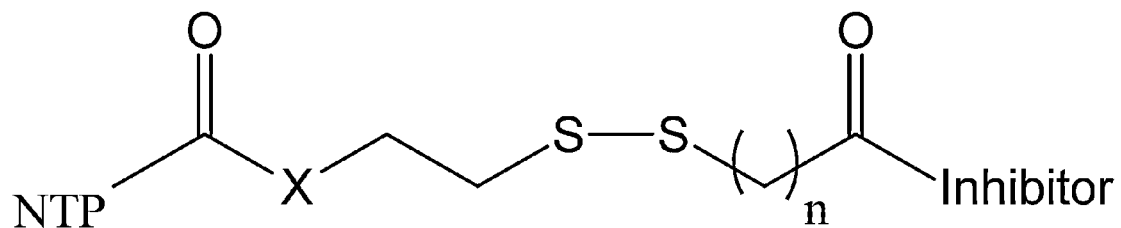
FIG. 14 shows an exemplary nucleotide analog with a cleavable linker comprising a variable number of methylene bridges.

The methods of the invention can be practiced under a variety of reaction conditions, however the orderly construction and recovery of desired polynucleotides will, in most cases, require a solid support to which the polynucleotides can be grown. In some embodiments, the methods include the enzymatically-mediated synthesis of polynucleotides on a solid support, as illustrated in FIG. 7. When used in conjunction with the NTP, linker, inhibitor analogs discussed above, it is possible to construct specific polynucleotide sequences of DNA as well as RNA by using, for example, TdT or poly(A) polymerase in an aqueous environment. As shown in FIG. 13, the TdT can be used to effect the stepwise construction of custom polynucleotides by extending the polynucleotide sequence a stepwise fashion. As discussed previously, the inhibitor group of each NTP analog causes the enzyme to stop with the addition of a nucleotide. After each nucleotide extension step, the reactants are washed away from the solid support prior to the removal of the inhibitor by cleaving the linker, and then new reactants are added, allowing the cycle to start anew. At the conclusion of n cycles of extension-remove-deblocking-wash, the finished full-length, single-strand polynucleotide is complete and can be cleaved from the solid support and recovered for subsequent use in applications such as DNA sequencing or PCR. Alternatively, the finished, full-length, single-strand polynucleotide can remain attached to the solid support for subsequent use in applications such as hybridization analysis, protein or DNA affinity capture. In other embodiments, partially double-stranded DNA can be used as an initiator, resulting in the synthesis of double-stranded polynucleotides.

Solid supports suitable for use with the methods of the invention may include glass and silica supports, including beads, slides, pegs, or wells. In some embodiments, the support may be tethered to another structure, such as a polymer well plate or pipette tip. In some embodiments, the solid support may have additional magnetic properties, thus allowing the support to be manipulated or removed from a location using magnets. In other embodiments, the solid support may be a silica coated polymer, thereby allowing the formation of a variety of structural shapes that lend themselves to automated processing.

Synthesizers

To capitalize on the efficiency of the disclosed methods, an aqueous phase DNA synthesizer can be constructed to produce desired polynucleotides in substantial quantities. In one embodiment, a synthesizer will include four wells of the described NTP analog reagents, i.e., dCTP, dATP, dGTP, and dTTP, as well as TdT at concentrations sufficient to effect polynucleotide growth. A plurality of initiating sequences can be attached to a solid support that is designed to be repeatedly dipped into each of the four wells, e.g., using a laboratory robot. The robot could be additionally programmed to rinse the solid support in wash buffer between nucleotide additions, cleave the linking group by exposing the support to a deblocking agent, and wash the solid support a second time prior to moving the solid support to the well of the next desired nucleotide. With simple programming, it is possible to create useful amounts of desired nucleotide sequences in a matter of hours, and with substantial reductions hazardous waste. Ongoing synthesis under carefully controlled conditions will allow the synthesis of polynucleotides with lengths in the thousands of base pairs. Upon completion, the extension products are released from the solid support, whereupon they can be used as finished nucleotide sequences.

A highly parallel embodiment could consist of a series of initiator-solid supports on pegs in either 96 or 384 well formats that could be individually retracted or lowered so that the pegs can be indexed to contact the liquids in the wells in a controlled fashion. The synthesizer could thus consist of the randomly addressable peg device, four enzyme-dNTP analog reservoirs in the same format as the peg device (96 or 384 spacing), additional reagent reservoirs (washing, deblocking, etc.) in the same format as the peg device (96 or 384 spacing), and a transport mechanism (e.g., a laboratory robot) for moving the peg device from one reservoir to another in a user programmable controlled but random access fashion. Care must be taken to avoid contaminating each of the four enzyme-dNTP reservoirs since the contents are reused throughout the entire synthesis process to reduce the cost of each polynucleotide synthesis.

In alternative embodiments, the reagents (e.g., nucleotide analogs, enzymes, buffers) will be moved between solid supports, allowing the reagents to be recycled. For example a system of reservoirs and pumps can move four different nucleotide analog solutions, wash buffers, and/or reducing agent solutions between one or more reactors in which the oligonucleotides will be formed. The reactors and pumps can be conventional, or the devices may be constructed using microfluidics. Because of the non-anhydrous (aqueous) nature of the process, no special care needs to be taken in the design of the hardware used to eliminate exposure to water. The synthesis process can take place with only precautions to control evaporative loss. A highly parallel embodiment could consist of a monolithic series of initiator-solid supports on pegs in either 96 or 384 well format that can be interfaced to a series of wells in the same matching format. Each well would actually be a reaction chamber that is fed by four enzyme-dNTP analog reservoirs and additional reagent reservoirs (washing, deblocking, etc.) with appropriate valves. Provisions would be made in the fluidics logic to recover the enzyme-dNTP reactants in a pristine fashion after each extension reaction since they are reused throughout the entire synthesis process to reduce the cost of each polynucleotide synthesis. In other embodiments, a system of pipetting tips could be used to add and remove reagents.

Figure 17:
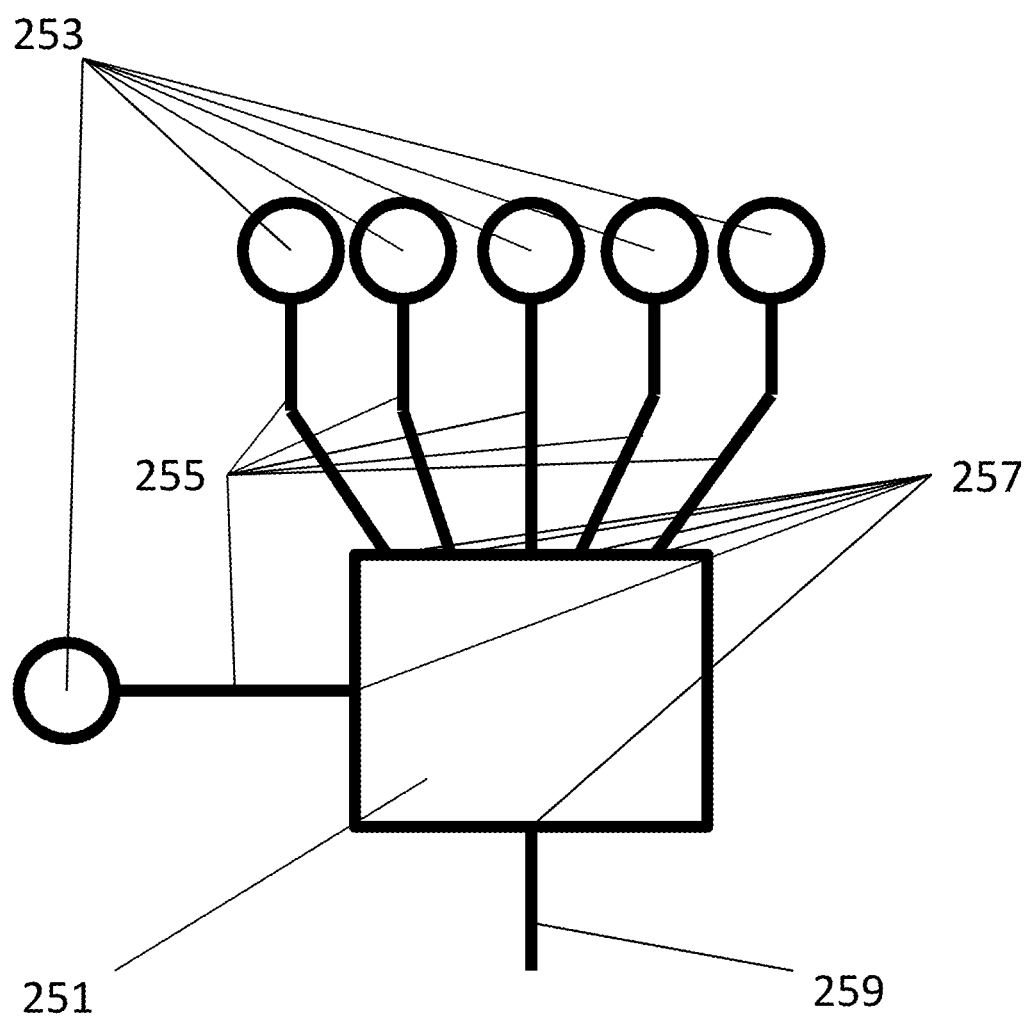
FIG. 17 shows an exemplary microfluidic polynucleotide synthesis device.

In certain aspects, polynucleotides may be synthesized using microfluidic devices and/or inkjet printing technology. An exemplary microfluidic polynucleotide synthesis device is shown in FIG. 17 for illustrative purposes and not to scale. Microfluidic channels 255, including regulators 257, couple reservoirs 253 to a reaction chamber 251 and an outlet channel 259, including a regulator 257 can evacuate waste from the reaction chamber 251. Microfluidic devices for polynucleotide synthesis may include, for example, channels 255, reservoirs 253, and/or regulators 257. Polynucleotide synthesis may occur in a microfluidic reaction chamber 251 which may include a number of anchored synthesized nucleotide initiators which may include beads or other substrates anchored or bound to an interior surface of the reaction chamber and capable of releasably bonding a NTP analog or polynucleotide initiator. The reaction chamber 251 may include at least one intake and one outlet channel 259 so that reagents may be added and removed to the reaction chamber 251. The microfluidic device may include a reservoir 253 for each respective NTP analog. Each of these NTP analog reservoirs 253 may also include an appropriate amount of TdT or any other enzyme which elongates DNA or RNA strands without template direction. Additional reservoirs 253 may contain reagents for linker/inhibitor cleavage and washing. These reservoirs 253 can be coupled to the reaction chamber 251 via separate channels 255 and reagent flow through each channel 255 into the reaction chamber 251 may be individually regulated through the use of gates, valves, pressure regulators, or other means. Flow out of the reaction chamber 251, through the outlet channel 259, may be similarly regulated.

In certain instances, reagents may be recycled, particularly the NTP analog-enzyme reagents. Reagents may be drawn back into their respective reservoirs 253 from the reaction chamber 251 via the same channels 255 through which they entered by inducing reverse flow using gates, valves, pressure regulators or other means. Alternatively, reagents may be returned from the reaction chamber 251 to their respective reservoirs 253 via independent return channels. The microfluidic device may include a controller capable of operating the gates, valves, pressure, or other regulators 257 described above.

An exemplary microfluidic polynucleotide synthesis reaction may include flowing a desired enzyme-NTP analog reagent into the reaction chamber 251; after a set amount of time, removing the enzyme-NTP analog reagent from the reaction chamber 251 via an outlet channel 259 or a return channel; flowing a wash reagent into the reaction chamber 251; removing the wash reagent from the reaction chamber 251 through an outlet channel 259; flowing a de-blocking or cleavage reagent into the reaction chamber 251; removing the de-blocking or cleavage reagent from the reaction chamber 251 via an outlet channel 259 or a return channel; flowing a wash reagent into the reaction chamber 251; removing the wash reagent from the reaction chamber 251 through an outlet channel 259; flowing the enzyme-NTP analog reagent including the next NTP in the desired sequence to be synthesized into the reaction chamber 251; and repeating until the desired polynucleotide has been synthesized. After the desired polynucleotide has been synthesized, it may be released from the reaction chamber anchor or substrate and collected via an outlet channel 259 or other means.

In certain aspects, reagents and compounds, including NTP analogs, TdT and/or other enzymes, and reagents for linker/inhibitor cleavage and/or washing may be deposited into a reaction chamber using inkjet printing technology or piezoelectric drop-on-demand (DOD) inkjet printing technology. Inkjet printing technology can be used to form droplets, which can be deposited, through the air, into a reaction chamber. Reagent droplets may have volumes in the picoliter to nanoliter scale. Droplets may be introduced using inkjet printing technology at a variety of frequencies including 1 Hz, 10, Hz, 100 Hz, 1 kHz, 2 kHz, and 2.5 kHz. Various reagents may be stored in separate reservoirs within the inkjet printing device and the inkjet printing device may deliver droplets of various reagents to various discrete locations including, for example, different reaction chambers or wells within a chip. In certain embodiments, inkjet and microfluidic technologies may be combined wherein certain reagents and compounds are delivered to the reaction chamber via inkjet printing technology while others are delivered via microfluidic channels or tubes. An inkjet printing device may be controlled by a computing device comprising at least a non-transitory, tangible memory coupled to a processor. The computing device may be operable to receive input from an input device including, for example, a touch screen, mouse, or keyboard and to control when and where the inkjet printing device deposits a droplet of reagent, the reagent it deposits, and/or the amount of reagent deposited.

In certain instances, a desired polynucleotide sequence may be entered into the computing device through an input device wherein the computing device is operable to perform the necessary reactions to produce the desired polynucleotide sequence by sequentially depositing the appropriate NTP analog, enzyme, cleavage reagent, and washing reagent, in the appropriate order as described above.

After synthesis, the released extension products can to be analyzed by high resolution PAGE to determine if the initiators have been extended by the anticipated number of bases compared to controls. A portion of the recovered synthetic DNA may also be sequenced to determine if the synthesized polynucleotides are of the anticipated sequence.

Because the synthesizers are relatively simple and do not require the toxic components needed for phosphoramidite synthesis, synthesizers of the invention will be widely accessible for research institutions, biotechs, and hospitals. Additionally, the ability to reuse/recycle reagents will reduce the waste produced and help reduce the costs of consumables. The inventors anticipate that the methods and systems will be useful in a number of applications, such as DNA sequencing, PCR, and synthetic biology.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for synthesizing an oligonucleotide, comprising:

exposing an oligonucleotide attached to a solid support to a nucleotide analog in the presence of a nucleotidyl transferase enzyme and in the absence of a nucleic acid template such that the nucleotide analog is incorporated into the oligonucleotide,
wherein the nucleotide analog comprises a nucleotide coupled, by a cleavable linker, to an inhibitor comprising a negatively-charged moiety and an amino acid with a negative charge that prevents the nucleotidyl transferase from catalyzing incorporation of a nucleotide or an additional nucleotide analog into said oligonucleotide until said inhibitor is removed by cleavage of said cleavable linker.

2. The method of claim 1, wherein the nucleotide analog comprises the following structure:

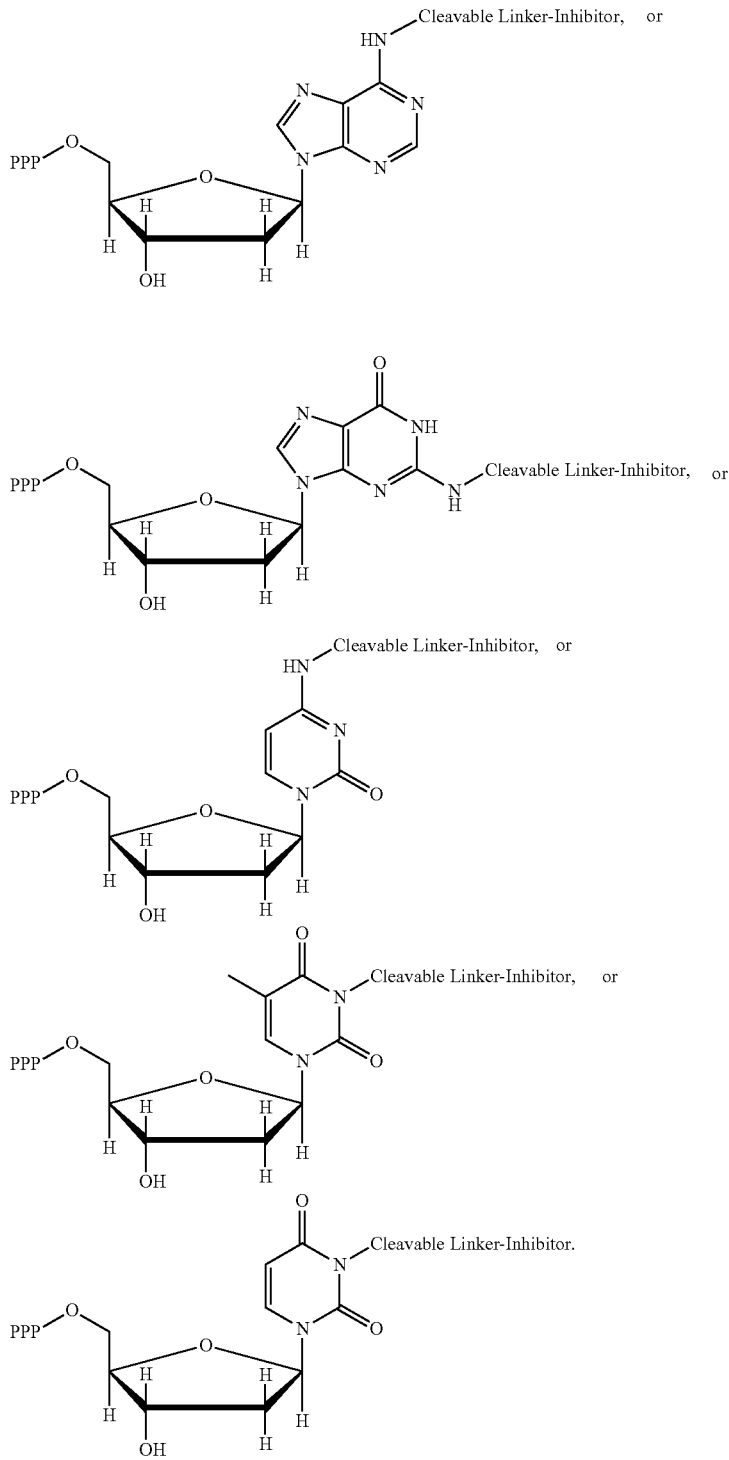

3. The method of claim 1, wherein the nucleotide analog comprises the following structure:

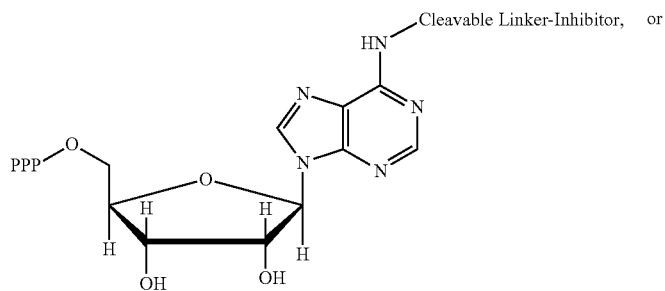
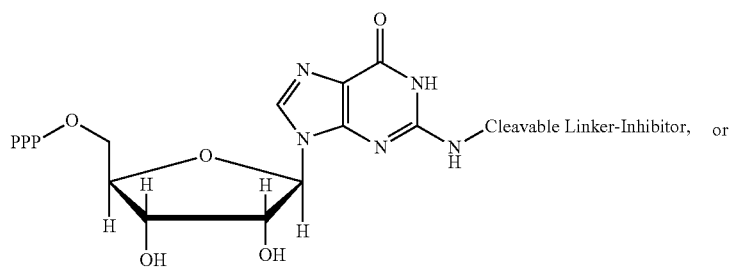
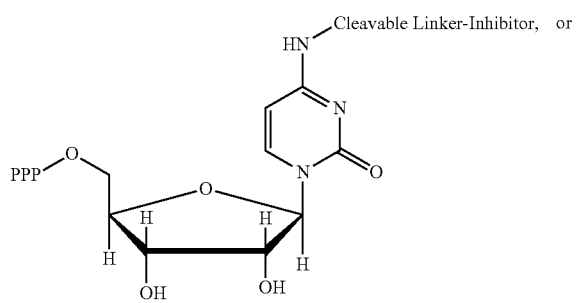
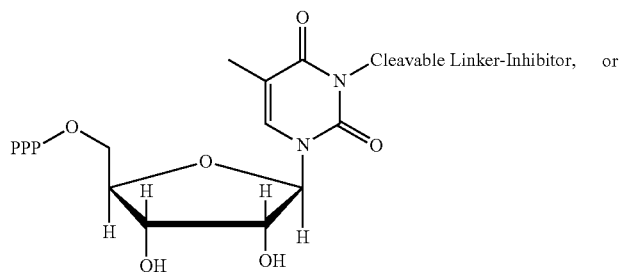
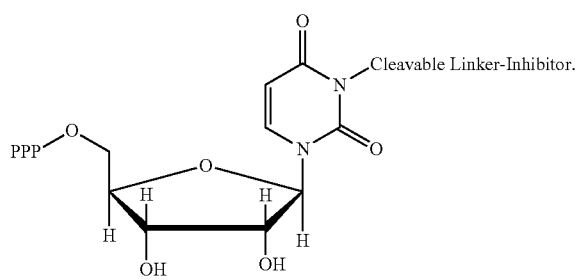

4. The method of claim 1, wherein the nucleotide analog comprises the following cleavable linker structure:

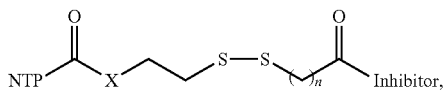

wherein NTP=nucleotide triphosphate, n=1, 2, 3, or 4, and —X— is —O—, —S—, —NH—, or —CH$_2$—.

5. The method of claim 1, wherein the nucleotide analog has the following cleavable linker structure:

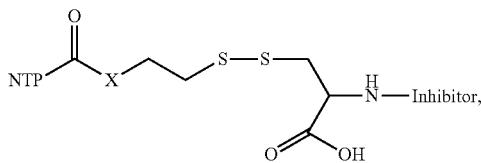

wherein NTP=nucleotide triphosphate, —X— is —O—, —S—, —NH—, or —CH$_2$—.

6. The method of claim 1, wherein the nucleotide analog has the following inhibitor structure:

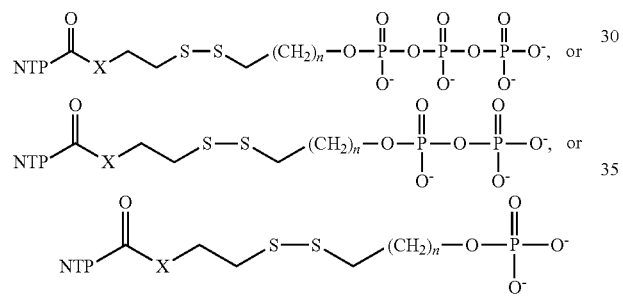

wherein NTP=nucleotide triphosphate, n=1, 2, 3, or 4, and —X— is —O—, —S—, —NH—, or —CH$_2$—.

7. The method of claim 1, wherein the nucleic acid attached to the solid support is exposed to the nucleotide analog in the presence of an aqueous solution having a pH between about 6.5 and 8.5.

8. The method of claim 1, the nucleic acid attached to the solid support is exposed to the nucleotide analog in the presence of an aqueous solution at a temperature between about 35 and 39° C.

9. The method of claim 1, wherein the solid support is a bead, a well, or a peg.

10. The method of claim 1, wherein the nucleic acid is single stranded.

11. The method of claim 1, wherein the cleavable linker comprises a moiety that forms a cyclic by-product when cleaved from the nucleotide analog.

12. The method of claim 1, further comprising:
cleaving the cleavable linker in order to produce a native nucleotide; and
exposing the native nucleotide to a second nucleotide analog in the presence of a nucleotidyl transferase enzyme and in the absence of a nucleic acid template.

13. The method of claim 1, further comprising providing an aqueous solution comprising the nucleotide analog and the nucleotidyl transferase enzyme.

14. The method of claim 1, wherein the amino acid is acetylated.

15. The method of claim 1, wherein the nucleotide analog comprises a ribose sugar or a deoxyribose sugar.

16. The method of claim 1, wherein the nucleotide substrate comprises a base selected from the group consisting of adenine, guanine, cytosine, thymine, and uracil.

17. The method of claim 1, wherein the nucleotide analog is encapsulated in a droplet.

18. The method of claim 1, wherein the nucleotidyl transferase enzyme is encapsulated in a droplet.

19. A method for synthesizing an oligonucleotide, comprising:
exposing an oligonucleotide attached to a solid support to a nucleotide analog in the presence of a nucleotidyl transferase enzyme and in the absence of a nucleic acid template such that the nucleotide analog is incorporated into the oligonucleotide,
wherein the nucleotide analog comprises a nucleotide coupled, by a cleavable linker, to an inhibitor comprising a positively-charged moiety and an amino acid with a positive charge that prevents the nucleotidyl transferase from catalyzing incorporation of a nucleotide or an additional nucleotide analog into said oligonucleotide until said inhibitor is removed by cleavage of said cleavable linker.

20. The method of claim 19, wherein the nucleotide analog comprises the following structure:

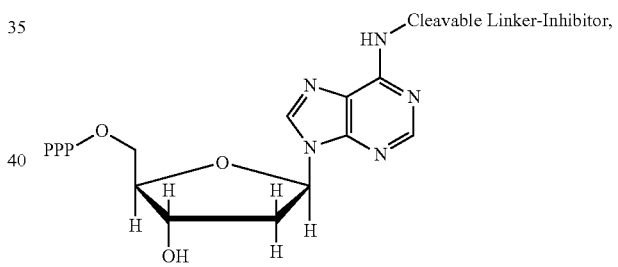

or

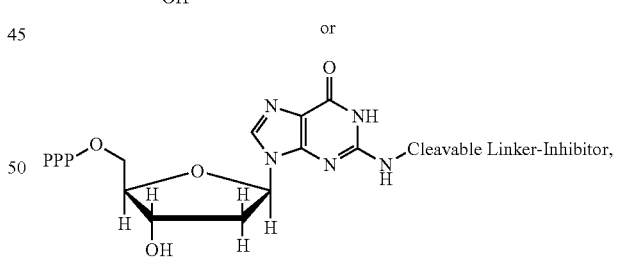

or

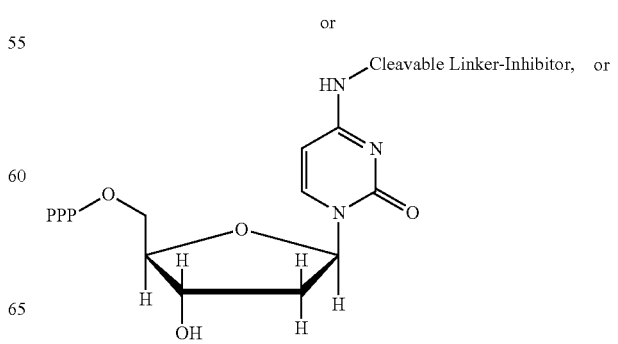

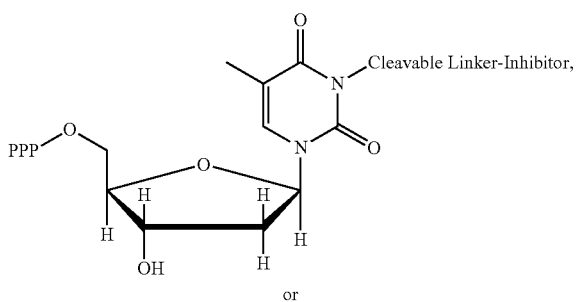

or

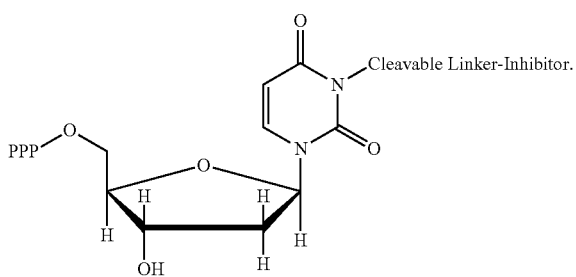

21. The method of claim 19, wherein the nucleotide analog comprises the following structure:

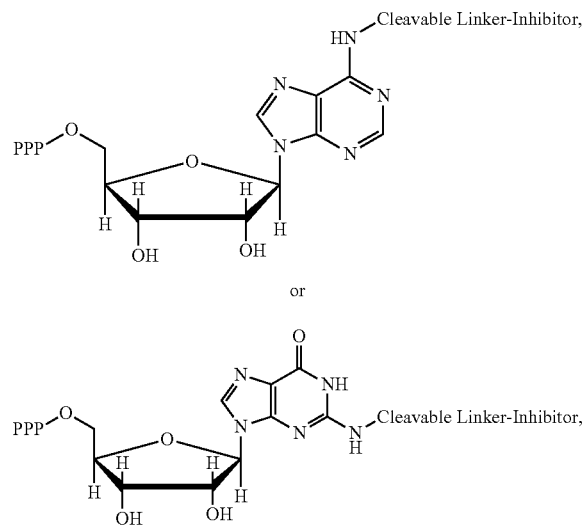

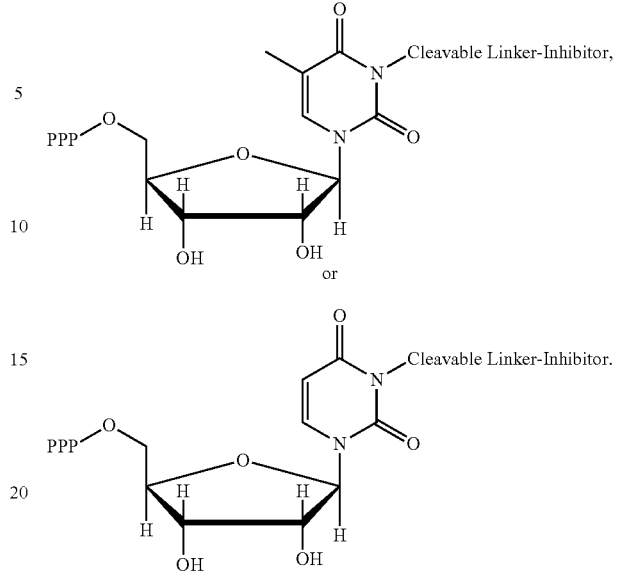

22. The method of claim 19, wherein the nucleotide analog comprises the following cleavable linker structure:

wherein NTP=nucleotide triphosphate, n=1, 2, 3, or 4, and —X— is —O—, —S—, —NH—, or —CH$_2$—.

23. The method of claim 19, wherein the nucleotide analog has the following cleavable linker structure:

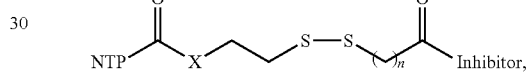

wherein NTP=nucleotide triphosphate, —X— is —O—, —S—, —NH—, or —CH$_2$—.

24. The method of claim 19, wherein the nucleotide analog has the following inhibitor structure:

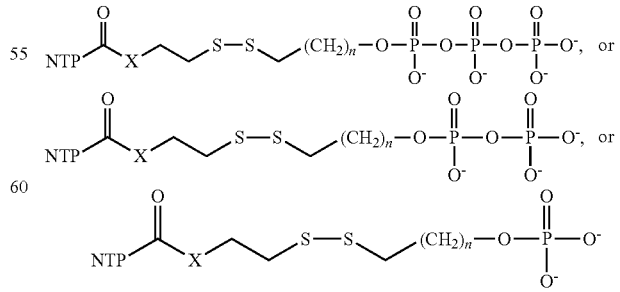

wherein NTP=nucleotide triphosphate, n=1, 2, 3, or 4, and —X— is —O—, —S—, —NH—, or —CH$_2$—.

25. The method of claim 19, wherein the nucleic acid attached to the solid support is exposed to the nucleotide analog in the presence of an aqueous solution having a pH between about 6.5 and 8.5.

26. The method of claim 19, the nucleic acid attached to the solid support is exposed to the nucleotide analog in the presence of an aqueous solution at a temperature between about 35 and 39° C.

27. The method of claim 19, wherein the solid support is a bead, a well, or a peg.

28. The method of claim 19, wherein the nucleic acid is single stranded.

29. The method of claim 19, wherein the cleavable linker comprises a moiety that forms a cyclic by-product when cleaved from the nucleotide analog.

30. The method of claim 19, further comprising:
cleaving the cleavable linker in order to produce a native nucleotide; and
exposing the native nucleotide to a second nucleotide analog in the presence of a nucleotidyl transferase enzyme and in the absence of a nucleic acid template.

31. The method of claim 19, further comprising providing an aqueous solution comprising the nucleotide analog and the nucleotidyl transferase enzyme.

32. The method of claim 19, wherein the amino acid is acetylated.

33. The method of claim 19, wherein the nucleotide analog comprises a ribose sugar or a deoxyribose sugar.

34. The method of claim 19, wherein the nucleotide substrate comprises a base selected from the group consisting of adenine, guanine, cytosine, thymine, and uracil.

35. The method of claim 19, wherein the nucleotide analog is encapsulated in a droplet.

36. The method of claim 19, wherein the nucleotidyl transferase enzyme is encapsulated in a droplet.

37. A method for synthesizing an oligonucleotide, comprising:
exposing an oligonucleotide attached to a solid support to a nucleotide analog in the presence of a nucleotidyl transferase enzyme and in the absence of a nucleic acid template such that the nucleotide analog is incorporated into the oligonucleotide,
wherein the nucleotide analog has the following inhibitor structure:

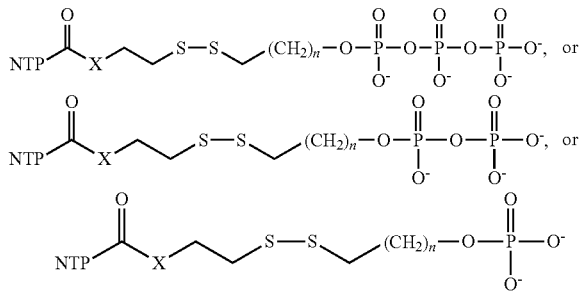

wherein NTP=nucleotide triphosphate, n=1, 2, 3, or 4, and
—X— is —O—, —S—, —NH—, or —CH$_2$—.

38. The method of claim 37, wherein the nucleic acid attached to the solid support is exposed to the nucleotide analog in the presence of an aqueous solution having a pH between about 6.5 and 8.5.

39. The method of claim 37, the nucleic acid attached to the solid support is exposed to the nucleotide analog in the presence of an aqueous solution at a temperature between about 35 and 39° C.

40. The method of claim 37, wherein the solid support is a bead, a well, or a peg.

41. The method of claim 37, wherein the nucleic acid is single stranded.

42. The method of claim 37, further comprising:
cleaving the cleavable linker in order to produce a native nucleotide; and
exposing the native nucleotide to a second nucleotide analog in the presence of a nucleotidyl transferase enzyme and in the absence of a nucleic acid template.

43. The method of claim 37, further comprising providing an aqueous solution comprising the nucleotide analog and the nucleotidyl transferase enzyme.

44. The method of claim 37, wherein the nucleotide analog comprises a ribose sugar or a deoxyribose sugar.

45. The method of claim 37, wherein the nucleotide substrate comprises a base selected from the group consisting of adenine, guanine, cytosine, thymine, and uracil.

46. The method of claim 37, wherein the nucleotide analog is encapsulated in a droplet.

47. The method of claim 37, wherein the nucleotidyl transferase enzyme is encapsulated in a droplet.

* * * * *